(12) United States Patent
Saxena et al.

(10) Patent No.: US 12,204,142 B2
(45) Date of Patent: *Jan. 21, 2025

(54) ARRAYS OF INTEGRATED ANALYTICAL DEVICES AND METHODS FOR PRODUCTION

(71) Applicant: Pacific Biosciences of California, Inc., Menlo Park, CA (US)

(72) Inventors: Ravi Saxena, Millbrae, CA (US); Michael Tzu Ru, San Mateo, CA (US); Takashi Whitney Orimoto, Sunnyvale, CA (US); Annette Grot, Cupertino, CA (US); Mathieu Foquet, Newark, CA (US); Hou-Pu Chou, Sunnyvale, CA (US)

(73) Assignee: PACIFIC BIOSCIENCES OF CALIFORNIA, INC., Menlo Park, CA (US)

( * ) Notice: Subject to any disclaimer, the term of this patent is extended or adjusted under 35 U.S.C. 154(b) by 1050 days.

This patent is subject to a terminal disclaimer.

(21) Appl. No.: 17/012,966

(22) Filed: Sep. 4, 2020

(65) Prior Publication Data

US 2021/0124115 A1 Apr. 29, 2021

Related U.S. Application Data

(63) Continuation of application No. 16/430,134, filed on Jun. 3, 2019, now Pat. No. 10,768,362, which is a continuation of application No. 15/953,792, filed on Apr. 16, 2018, now Pat. No. 10,310,178, which is a continuation of application No. 15/600,668, filed on May 19, 2017, now Pat. No. 9,946,017, which is a continuation of application No. 15/158,756, filed on May 19, 2016, now Pat. No. 9,658,161, which is a
(Continued)

(51) Int. Cl.
| | |
|---|---|
| *G02B 6/12* | (2006.01) |
| *B29D 11/00* | (2006.01) |
| *B29D 17/00* | (2006.01) |
| *C12Q 1/6869* | (2018.01) |
| *G01N 21/64* | (2006.01) |
| *G02B 5/18* | (2006.01) |
| *G02B 6/02* | (2006.01) |
| *G02B 6/124* | (2006.01) |
| *G02B 6/136* | (2006.01) |
| *B29L 11/00* | (2006.01) |
| *G01N 21/77* | (2006.01) |

(52) U.S. Cl.
CPC ...... *G02B 6/12004* (2013.01); *B29D 11/0073* (2013.01); *B29D 17/007* (2013.01); *C12Q 1/6869* (2013.01); *G01N 21/6454* (2013.01); *G01N 21/648* (2013.01); *G02B 5/189* (2013.01); *G02B 6/02123* (2013.01); *G02B 6/12002* (2013.01); *G02B 6/124* (2013.01); *G02B 6/136* (2013.01); *B29L 2011/005* (2013.01); *B29L 2011/0066* (2013.01); *B29L 2011/0075* (2013.01); *G01N 2021/6467* (2013.01); *G01N 2021/6471* (2013.01); *G01N 2021/6478* (2013.01); *G01N 2021/7713* (2013.01); *G01N 2201/0873* (2013.01); *G02B 2006/12038* (2013.01); *G02B 2006/12109* (2013.01)

(58) Field of Classification Search
CPC ............ G02B 6/12004; G02B 5/189; G02B 6/02123; G02B 6/12002; G02B 6/124; G02B 6/136; G02B 2006/12038; G02B 2006/121; B29D 11/0073; B29D 17/007; C12Q 1/6869; G01N 21/6454; G01N 21/648; G01N 2021/6467; G01N 2021/6471; G01N 2021/6478; G01N 2021/7713; G01N 2201/0873; B29L 2011/005; B29L 2011/0066; B29L 2011/0075

See application file for complete search history.

(56) References Cited

U.S. PATENT DOCUMENTS

| | | |
|---|---|---|
| 4,645,523 A | 2/1987 | Howard et al. |
| 5,082,629 A | 1/1992 | Burgess, Jr. et al. |

(Continued)

FOREIGN PATENT DOCUMENTS

| | | |
|---|---|---|
| EP | 1105529 B1 | 11/2005 |
| EP | 1871902 B1 | 10/2010 |

(Continued)

OTHER PUBLICATIONS

Blazej et al, Microfabricated bioprocessor for integrated nanoliter-scale Sanger DNA sequencing, PNAS, 103, 19, ,2006 (Year: 2006).*

(Continued)

*Primary Examiner* — Narayan K Bhat
(74) *Attorney, Agent, or Firm* — VLP Law Group LLP

(57) ABSTRACT

Arrays of integrated analytical devices and their methods for production are provided. The arrays are useful in the analysis of highly multiplexed optical reactions in large numbers at high densities, including biochemical reactions, such as nucleic acid sequencing reactions. The integrated devices allow the highly sensitive discrimination of optical signals using features such as spectra, amplitude, and time resolution, or combinations thereof. The arrays and methods of the invention make use of silicon chip fabrication and manufacturing techniques developed for the electronics industry and highly suited for miniaturization and high throughput.

19 Claims, 22 Drawing Sheets

Related U.S. Application Data continuation of application No. 13/920,037, filed on Jun. 17, 2013, now Pat. No. 9,372,308.

(60) Provisional application No. 61/660,776, filed on Jun. 17, 2012.

(56) References Cited

U.S. PATENT DOCUMENTS

| | | |
|---|---|---|
| 5,094,517 A | 3/1992 | Franke |
| 5,135,876 A | 8/1992 | Andrade et al. |
| 5,157,262 A | 10/1992 | Marsoner et al. |
| 5,159,661 A | 10/1992 | Ovshinsky et al. |
| 5,173,747 A | 12/1992 | Boiarski et al. |
| 5,192,502 A | 3/1993 | Attridge et al. |
| 5,233,673 A | 8/1993 | Vali et al. |
| 5,239,178 A | 8/1993 | Derndinger et al. |
| 5,439,647 A | 8/1995 | Saini |
| 5,446,534 A | 8/1995 | Goldman |
| 5,470,710 A | 11/1995 | Weiss et al. |
| 5,545,531 A | 8/1996 | Rava et al. |
| 5,578,832 A | 11/1996 | Trulson et al. |
| 5,605,662 A | 2/1997 | Heller et al. |
| 5,631,734 A | 5/1997 | Stern et al. |
| 5,677,196 A | 10/1997 | Herron et al. |
| 5,695,934 A | 12/1997 | Brenner |
| 5,744,305 A | 4/1998 | Fodor et al. |
| 5,793,913 A * | 8/1998 | Kovacic ............... G02B 6/42 257/13 |
| 5,812,709 A | 9/1998 | Arai et al. |
| 5,821,058 A | 10/1998 | Smith et al. |
| 5,832,165 A | 11/1998 | Reichert et al. |
| 5,867,266 A | 2/1999 | Craighead |
| 5,919,712 A | 7/1999 | Herron et al. |
| 6,002,520 A | 12/1999 | Hoch et al. |
| 6,071,748 A | 6/2000 | Modlin et al. |
| 6,192,168 B1 | 2/2001 | Feldstein et al. |
| 6,210,896 B1 | 4/2001 | Chan |
| 6,236,945 B1 | 5/2001 | Simpson et al. |
| 6,263,286 B1 | 7/2001 | Gilmanshin et al. |
| 6,287,871 B1 * | 9/2001 | Herron ............ G01N 33/54373 422/82.11 |
| 6,325,977 B1 | 12/2001 | Theil |
| 6,388,788 B1 | 5/2002 | Harris et al. |
| 6,437,345 B1 | 8/2002 | Bruno-Raimondi et al. |
| 6,438,279 B1 | 8/2002 | Craighead et al. |
| 6,603,537 B1 | 8/2003 | Dietz et al. |
| 6,611,634 B2 | 8/2003 | Herron et al. |
| 6,690,002 B2 | 2/2004 | Kuroda et al. |
| 6,699,655 B2 | 3/2004 | Nikiforov |
| 6,784,982 B1 | 8/2004 | Blumenfeld et al. |
| 6,800,860 B2 | 10/2004 | Dietz et al. |
| 6,818,395 B1 | 11/2004 | Quake et al. |
| 6,867,851 B2 | 3/2005 | Blumenfeld et al. |
| 6,917,726 B2 | 7/2005 | Levene et al. |
| 6,919,211 B1 | 7/2005 | Fodor et al. |
| 6,979,830 B2 | 12/2005 | Dietz et al. |
| 6,982,146 B1 | 1/2006 | Schneider et al. |
| 6,987,613 B2 | 1/2006 | Pocius et al. |
| 7,013,054 B2 | 3/2006 | Levene et al. |
| 7,022,515 B2 | 4/2006 | Herron et al. |
| 7,056,661 B2 | 6/2006 | Korlach et al. |
| 7,057,832 B2 | 6/2006 | Wu et al. |
| 7,075,695 B2 | 7/2006 | Gronbach |
| 7,081,954 B2 | 7/2006 | Sandstrom |
| 7,083,914 B2 | 8/2006 | Seul et al. |
| 7,130,041 B2 | 10/2006 | Bouzid et al. |
| 7,135,667 B2 | 11/2006 | Oldham et al. |
| 7,139,074 B2 | 11/2006 | Reel |
| 7,145,645 B2 | 12/2006 | Blumenfeld et al. |
| 7,150,997 B2 | 12/2006 | Kovacs |
| 7,170,050 B2 | 1/2007 | Turner et al. |
| 7,175,811 B2 | 2/2007 | Bach et al. |
| 7,181,122 B1 | 2/2007 | Levene et al. |
| 7,189,361 B2 | 3/2007 | Carson et al. |
| 7,197,196 B2 | 3/2007 | Lin et al. |
| 7,199,357 B1 | 4/2007 | Oldham et al. |
| 7,209,836 B1 | 4/2007 | Schermer et al. |
| 7,227,128 B2 | 6/2007 | Sagatelyan |
| RE39,772 E | 8/2007 | Herron et al. |
| 7,257,141 B2 | 8/2007 | Chua |
| 7,302,348 B2 | 11/2007 | Ghosh et al. |
| 7,315,019 B2 | 1/2008 | Turner et al. |
| 7,323,681 B1 | 1/2008 | Oldham et al. |
| 7,400,380 B2 | 7/2008 | Hahn |
| 7,499,094 B2 | 3/2009 | Kuriyama |
| 7,537,734 B2 | 5/2009 | Reichert et al. |
| 7,709,808 B2 | 5/2010 | Reel et al. |
| 7,767,441 B2 | 8/2010 | Chiou et al. |
| 7,811,810 B2 | 10/2010 | Chiou et al. |
| 7,817,281 B2 | 10/2010 | Kiesel et al. |
| 7,820,983 B2 | 10/2010 | Lundquist et al. |
| 7,834,329 B2 | 11/2010 | Lundquist et al. |
| 7,838,847 B2 | 11/2010 | Lundquist et al. |
| 7,907,800 B2 | 3/2011 | Foquet et al. |
| 8,053,742 B2 | 11/2011 | Lundquist et al. |
| 8,207,509 B2 | 6/2012 | Lundquist et al. |
| 8,247,216 B2 | 8/2012 | Zaccarin et al. |
| 8,274,040 B2 | 9/2012 | Zhong et al. |
| 8,411,375 B2 | 4/2013 | Lenchenkov |
| 8,465,699 B2 | 6/2013 | Fehr et al. |
| 8,467,061 B2 | 6/2013 | McCaffrey et al. |
| 8,471,219 B2 | 6/2013 | Lundquist et al. |
| 8,471,230 B2 | 6/2013 | Zhong et al. |
| 8,618,507 B1 | 12/2013 | Lundquist et al. |
| 8,649,011 B2 | 2/2014 | McCaffrey et al. |
| 8,906,320 B1 | 12/2014 | Eltoukhy et al. |
| 8,906,670 B2 | 12/2014 | Gray et al. |
| 9,029,802 B2 | 5/2015 | Lundquist et al. |
| 9,372,308 B1 * | 6/2016 | Saxena ............... G02B 6/124 |
| 9,658,161 B2 * | 5/2017 | Saxena ............... C12Q 1/6869 |
| 9,946,017 B2 * | 4/2018 | Saxena ............ B29D 11/0073 |
| 10,310,178 B2 * | 6/2019 | Saxena ............ B29D 11/0073 |
| 10,768,362 B2 * | 9/2020 | Saxena ............. B29D 17/007 |
| 2002/0034457 A1 | 3/2002 | Reichert et al. |
| 2002/0110839 A1 | 8/2002 | Bach et al. |
| 2002/0113213 A1 | 8/2002 | Amirkhanian et al. |
| 2002/0146047 A1 | 10/2002 | Bendett et al. |
| 2003/0044781 A1 | 3/2003 | Korlach et al. |
| 2003/0132406 A1 | 7/2003 | Waldhausl et al. |
| 2003/0138180 A1 | 7/2003 | Kondo et al. |
| 2003/0174324 A1 | 9/2003 | Sandstrom |
| 2003/0174992 A1 | 9/2003 | Levene et al. |
| 2004/0009612 A1 * | 1/2004 | Zhao ................ C12Q 1/6858 436/501 |
| 2004/0040868 A1 | 3/2004 | DeNuzzio et al. |
| 2004/0046128 A1 | 3/2004 | Abel et al. |
| 2004/0197793 A1 | 10/2004 | Hassibi et al. |
| 2004/0249227 A1 | 12/2004 | Klapproth et al. |
| 2005/0006607 A1 | 1/2005 | Winter et al. |
| 2005/0014178 A1 | 1/2005 | Holm-Kennedy |
| 2005/0135974 A1 | 6/2005 | Harvey et al. |
| 2005/0175273 A1 | 8/2005 | Iida et al. |
| 2005/0201899 A1 | 9/2005 | Weisbuch |
| 2005/0206895 A1 | 9/2005 | Salmelainen |
| 2005/0259910 A1 * | 11/2005 | Li ..................... G02B 6/12004 385/14 |
| 2006/0060766 A1 | 3/2006 | Turner et al. |
| 2006/0061754 A1 * | 3/2006 | Turner ................. G02B 6/13 356/38 |
| 2006/0103850 A1 | 5/2006 | Alphonse et al. |
| 2006/0205092 A1 * | 9/2006 | Lackritz .......... G01N 33/54373 436/525 |
| 2007/0036511 A1 | 2/2007 | Lundquist et al. |
| 2007/0099212 A1 | 5/2007 | Harris |
| 2007/0134128 A1 | 6/2007 | Korlach |
| 2007/0146701 A1 | 6/2007 | Kiesel et al. |
| 2007/0188746 A1 | 8/2007 | Kraus et al. |
| 2007/0196815 A1 | 8/2007 | Lappe et al. |
| 2008/0002929 A1 | 1/2008 | Bowers et al. |
| 2008/0020938 A1 | 1/2008 | Kaplan |
| 2008/0039339 A1 | 2/2008 | Hassibi et al. |
| 2008/0056950 A1 | 3/2008 | Weisbuch et al. |
| 2008/0161195 A1 | 7/2008 | Turner et al. |

(56) References Cited

U.S. PATENT DOCUMENTS

| | | |
|---|---|---|
| 2008/0176769 A1 | 7/2008 | Rank et al. |
| 2008/0212960 A1 | 9/2008 | Lundquist et al. |
| 2009/0146076 A1 | 6/2009 | Chiou et al. |
| 2009/0181396 A1 | 7/2009 | Luong et al. |
| 2009/0208957 A1 | 8/2009 | Korlach et al. |
| 2009/0247414 A1 | 10/2009 | Obradovic et al. |
| 2009/0311774 A1 | 12/2009 | Chiou et al. |
| 2010/0065726 A1 | 3/2010 | Zhong et al. |
| 2010/0099100 A1 | 4/2010 | Zaccarin et al. |
| 2010/0121582 A1 | 5/2010 | Pan et al. |
| 2010/0163521 A1 | 7/2010 | Balamane et al. |
| 2010/0255488 A1 | 10/2010 | Kong et al. |
| 2010/0256918 A1 | 10/2010 | Chen et al. |
| 2010/0295083 A1 | 11/2010 | Celler |
| 2011/0117637 A1 | 5/2011 | Gray et al. |
| 2011/0183409 A1 | 7/2011 | Newby et al. |
| 2011/0210094 A1 | 9/2011 | Gray et al. |
| 2011/0223590 A1 | 9/2011 | Chiou et al. |
| 2011/0306039 A1 | 12/2011 | Chiou et al. |
| 2012/0014837 A1 | 1/2012 | Fehr et al. |
| 2012/0019828 A1 | 1/2012 | McCaffrey et al. |
| 2012/0021525 A1 | 1/2012 | Fehr et al. |
| 2012/0052506 A1 | 3/2012 | Yue et al. |
| 2012/0058469 A1 | 3/2012 | Shen |
| 2012/0058473 A1 | 3/2012 | Yue et al. |
| 2012/0058482 A1 | 3/2012 | Shen et al. |
| 2012/0077189 A1 | 3/2012 | Shen et al. |
| 2012/0085894 A1* | 4/2012 | Zhong .................. C12Q 1/6825 385/14 |
| 2012/0156100 A1 | 6/2012 | Tsai et al. |
| 2013/0043552 A1 | 2/2013 | Lazarov et al. |
| 2013/0251592 A1 | 9/2013 | McCaffrey et al. |
| 2014/0241682 A1 | 8/2014 | Sandhu et al. |

FOREIGN PATENT DOCUMENTS

| | | |
|---|---|---|
| EP | 2362209 B1 | 10/2015 |
| KR | 20050088782 A | 9/2005 |
| WO | 1991006678 A1 | 5/1991 |
| WO | 2001016375 A2 | 3/2001 |
| WO | 2004100068 A2 | 11/2004 |
| WO | 2006116726 A2 | 11/2006 |
| WO | 2006135782 A2 | 12/2006 |
| WO | 2007002367 A2 | 1/2007 |
| WO | 2007011549 A1 | 1/2007 |
| WO | 2008002765 A2 | 1/2008 |
| WO | 2009056065 A1 | 5/2009 |
| WO | 2009131535 A1 | 10/2009 |
| WO | 2009149125 A2 | 12/2009 |
| WO | 2010051773 A1 | 5/2010 |
| WO | 2010102567 A1 | 9/2010 |
| WO | 2011076132 A2 | 6/2011 |
| WO | 2014031157 A1 | 2/2014 |

OTHER PUBLICATIONS

Abbas et al. (2011) Sens. Actuators B Chem. 156:169-175.
Barrios (2006) IEEE Photon Technol. Lett. 18:2419.
Barrios et al. (2007) Optics Letters 32:3080.
Barrios et al. (2008) Optics Letters 33:708.
Bernini et al. (2005) Proc. SPIE 5728:101-111.
Boiarski et al. (1992) Proc. SPIE 1793:199-211.
Budach et al. (1999) Anal. Chem. 71(16):3347-3355.
Chen et al. (2012) Optics Letters 37:2814.
Cottier et al. (2002) Proc. SPIE 4616:53-63.
Deopura, M. et al. (2001) Optics Lett 26(15):1197-1199.
Duveneck et al. (2002) Anal Chem Acta 469:49-61.
Eid et al. (2009) Science 323:133.
Feldstein et al. (1999) J. Biomed Microdev. 1:139-153.
Feng et al. (2006) IEEE J. Quantum Electron. 42:885.
Feng et al. (2007) Optics Letters 32:2131.
Fink, Y. et al. (1998) Science 282:1679-1682.
Fonollosa et al. (2006) Proceedings of SPIE 61860R-1: 61860R-11.
Herron et al. (2003) Biopolymers at Interfaces 2nd Ed, Surfactant Science Series vol. 110, Marcel Dekker, NY pp. 115-163.
Laurell et al. (2012) Optics Express 20:22308.
Levene, M.J. et al. (2003) Science 299:682-686.
Mortazavi et al. (1994) Optics Letters 19:1290.
Nava et al. (2010) Electronics Letters 46:1686.
Pan et al. (2011) Optics Communications 284:429.
Psaltis et al. (2006) Nature 442:381.
Robinson et al. (2008) Optics Express 16:4296.
Sahin et al. (2011) J. Nanophoton. 5:051812.
Salama et al. (2004) Biosensors & Bioelectronics 19:1377-1386.
Song et al. (2012) Optics Express 20:22290.
Sun et al. (2007) Optics Express 15:17967.
Weissman et al. (1999) Proc. SPIE 3596:210-216.
Wu et al. (2006) Biosensors and Bioelectronics 21:1252-1263.
Yao et al. (2012) Nonlinear Optics and Solid-State Lasers, Springer-Verlag Berlin Heidelberg, Chapter 5.
Yariv, A. et al. (1977) IEEE J Quantum Elec QE-13(4):233-253.

* cited by examiner

| No. | Mask No. | Material | Process | Stage Name | Tool Type | sketch map |
|---|---|---|---|---|---|---|
| 1 | NA | CMOS Image Sensor Wafer | Clean | Substrate clean | CLN | |
| 2 | NA | SiON | PECVD | Passivation deposition | DEP | |
| 3 | NA | TiO2/SiO2 etc | ALD | Filter deposition | DEP | |
| 4 | NA | SiO2 | PECVD | Collection cone deposition | DEP | |
| 5 | 1 | PR (Photoresist) | I-Line | Cone patterning | LITH | |
| 6 | NA | SiO2 | Etch | Cone etching | ETCH | |
| 7 | NA | Al/Au | Deposition PVD | Reflective layer deposition | DEP | |
| 8 | NA | SiO2 | Spin Coat, PECVD | Gap Fill deposition | DEP | |
| 9 | 2 | PR | I-Line | Reverse etch patterning | LITH | |
| 10 | NA | SiO2 | Etch | Reverse pattern etching | ETCH | |
| 11 | NA | SiO2 | CMP | Planarization | PLN | |

Figure 18A

| 12 | 3 | PR | I-Line | Pattern definition for Top flat mirror etch (TFME) | LITH | 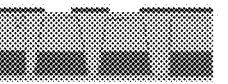 |
| --- | --- | --- | --- | --- | --- | --- |
| 13 | NA | Al/Au | Etch | TFME etch | ETCH | 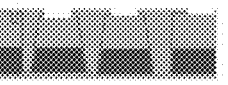 |
| 14 | NA | SOD, SiO2 | Spin Coat, PECVD | Bottom clad deposition | DEP |  |
| 15 | NA | Si3N4 | PECVD, ALD | Core deposition | DEP |  |
| 16 | 3 | PR | 248/I-Line | Pattern definition for waveguide | LITH |  |
| 17 | NA | Si3N4 | Etch | Etch core for waveguide definition | ETCH |  |
| 18 | NA | SOD, SiO2 | Spin Coat, PECVD | Top clad deposition | DEP |  |
| 19 | NA | Al | PVD | Confinement material deposition | DEP |  |
| 20 | 5 | PR | 193nm | Pattern definition for nanowell | LITH | 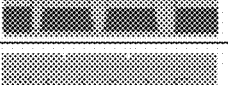 |
| 21 | NA | Al, SOG, SiO2 | 2 stage etch | Etch nanowell | ETCH |  |
| 22 | 4 | PR | I-Line | Pattern definition for deep trench opening | LITH | 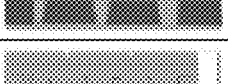 |
| 23 | NA | SiO2, Si3N4, PR | Deep Etch | Deep trench etch | ETCH |  |
| 24 | NA | PR/Barc | Clean | | CLN |  |

Figure 18B

| No. | Mask No. | Material | Process | Stage Name | Tool Type | sketch map |
|---|---|---|---|---|---|---|
| 1 | NA | CMOS Image Sensor Wafer | Clean | Substrate clean | CLN | |
| 2 | NA | SiON | PECVD | Passivation deposition | DEP | |
| 3 | NA | Epoxy Resin | Spin Coat | Filter deposition | DEP | |
| 4 | NA | SiO2 | PECVD | Collection cone deposition | DEP | |
| 5 | 1 | PR (Photoresist) | I-Line | Cone patterning | LITH | |
| 6 | NA | SiO2 | Etch | Cone etching | ETCH | |
| 7 | NA | Al/Au | Deposition PVD | Reflective layer deposition | DEP | |
| 8 | NA | SiO2 | Spin Coat, PECVD | Gap Fill deposition | DEP | |
| 9 | 2 | PR | I-Line | Reverse etch pattering | LITH | |
| 10 | NA | SiO2 | Etch | Reverse pattern etching | ETCH | |
| 11 | NA | SiO2 | CMP | Planarization | PLN | |

Figure 19A

| 12 | 3 | PR | I-Line | Pattern definition for Top flat mirror etch (TFME) | LITH | 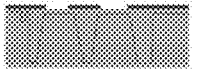 |
| --- | --- | --- | --- | --- | --- | --- |
| 13 | NA | Al/Au | Etch | TFME etch | ETCH |  |
| 14 | NA | SOD, SiO2 | Spin Coat, PECVD | Bottom clad deposition | DEP |  |
| 15 | NA | Si3N4 | PECVD, ALD | Core deposition | DEP |  |
| 16 | 3 | PR | 248/I-Line | Pattern definition for waveguide | LITH |  |
| 17 | NA | Si3N4 | Etch | Etch core for waveguide definition | ETCH | 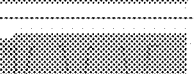 |
| 18 | NA | SOD, SiO2 | Spin Coat, PECVD | Top clad deposition | DEP | 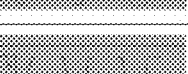 |
| 19 | NA | Al | PVD | Confinement material deposition | DEP |  |
| 20 | 5 | PR | 193nm | Pattern definition for nanowell | LITH | 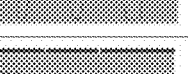 |
| 21 | NA | Al, SOG, SiO2 | 2 stage etch | Etch nanowell | ETCH | 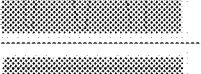 |
| 22 | 4 | PR | I-Line | Pattern definition for deep trench opening | LITH | 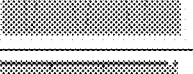 |
| 23 | NA | SiO2, Si3N4, PR | Deep Etch | Deep trench etch | ETCH | 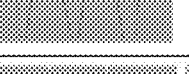 |
| 24 | NA | PR/Barc | Clean | | CLN |  |

Figure 19B

| No. | Mask No. | Material | Process | Stage Name | Tool Type | sketch map |
|---|---|---|---|---|---|---|
| 1 | NA | CMOS Image Sensor Wafer | Clean | Substrate clean | CLN | |
| 2 | NA | SiON | PECVD | Passivation deposition | DEP |  |
| 3 | NA | Thin film filter 1 | Spin Coat/ALD | Filter deposition | DEP | 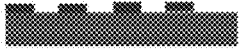 |
| 4 | 1 | Thin film filter 1 | I-line | Filter patterning | LITH |  |
| 5 | NA | Thin film filter 1 | I-Line | Filter etching | ETCH |  |
| 6 | NA | Thin film filter 2 | Spin Coat/ALD | Filter deposition | DEP |  |
| 7 | 2 | Thin film filter 2 | Etch | Liftoff | CLN |  |
| 8 | NA | Oxide | PECVD | Planarization deposition | DEP | |

Figure 20

ARRAYS OF INTEGRATED ANALYTICAL DEVICES AND METHODS FOR PRODUCTION

CROSS-REFERENCE TO RELATED APPLICATIONS

This application is a continuation of U.S. patent application Ser. No. 16/430,134, filed on Jun. 3, 2019, which is a continuation of U.S. patent application Ser. No. 15/953,792, filed on Apr. 16, 2018, now U.S. Pat. No. 10,310,178, which is a continuation of U.S. patent application Ser. No. 15/600,668, filed on May 19, 2017, now U.S. Pat. No. 9,946,017, which is a continuation of U.S. patent application Ser. No. 15/158,756, filed on May 19, 2016, now U.S. Pat. No. 9,658,161, which is a continuation of U.S. patent application Ser. No. 13/920,037, filed on Jun. 17, 2013, now U.S. Pat. No. 9,372,308, which claims the benefit under 35 U.S.C. § 119 (e) of U.S. Provisional Application No. 61/660,776, filed on Jun. 17, 2012, the disclosures of which are incorporated herein by reference in their entireties.

BACKGROUND OF THE INVENTION

In analytical systems, the ability to increase the number of analyses being carried out at any given time by a given system has been a key component to increasing the utility and extending the lifespan of such systems. In particular, by increasing the multiplex factor of analyses with a given system, one can increase the overall throughput of the system, thereby increasing its usefulness while decreasing the costs associated with that use.

In optical analyses, increasing multiplex often poses increased difficulties, as it may require more complex optical systems, increased illumination or detection capabilities, and new reaction containment strategies. In some cases, systems seek to increase multiplex by many fold, and even orders of magnitude, which further implicate these considerations. Likewise, in certain cases, the analytical environment for which the systems are to be used is so highly sensitive that variations among different analyses in a given system may not be tolerable. These goals are often at odds with a brute force approach of simply making systems bigger and of higher power, as such steps often give rise to even greater consequences, e.g., in inter reaction cross-talk, decreased signal to noise ratios resulting from either or both of lower signal and higher noise, and the like. It would therefore be desirable to provide analytical systems that have substantially increased multiplex for their desired analysis, and particularly for use in highly sensitive reaction analyses, and in many cases, to do so while minimizing negative impacts of such increased multiplex.

At the same time, there is a continuing need to increase the performance of analytical systems and reduce the cost associated with manufacturing and using the system. In particular, there is a continuing need to increase the throughput of analytical systems. There is a continuing need to reduce the size and complexity of analytical systems. There is a continuing need for analytical systems that have flexible configurations and are easily scalable.

SUMMARY OF THE INVENTION

The instant invention addresses these and other problems by providing in one aspect arrays of integrated analytical devices comprising:

a substrate layer;
a filter module layer disposed on the substrate layer;
a collection module layer disposed on or with the filter module layer;
a waveguide module layer disposed on the collection module layer;
a zero-mode waveguide module layer disposed on the waveguide module layer;
wherein the zero-mode waveguide module layer comprises a plurality of nanometer-scale apertures penetrating into the waveguide module layer.

In some embodiments, the substrate layer is a detector layer.

In specific embodiments, the substrate layer is a CMOS wafer detector layer.

In some embodiments, the filter module layer comprises a dielectric filter.

In other embodiments, the filter module layer comprises an absorptive filter.

In specific embodiments, the detector layer comprises a color-separation layer.

According to some embodiments, the plurality of nanometer-scale apertures is formed by etching, and the etching is stopped using an endpoint signal.

In specific embodiments, the waveguide module layer comprises an upper cladding of low n material disposed on a high n material, and at least one nanometer-scale aperture fully penetrates the upper cladding of low n material into the high n material. In more specific embodiments, the at least one nanometer-scale aperture is partially backfilled. In even more specific embodiments, the at least one nanometer-scale aperture is partially backfilled using atomic layer deposition or low pressure chemical vapor deposition. In some specific embodiments, the upper cladding of low n material is $SiO_2$, and in some specific embodiments, the high n material is $Si_3N_4$. In some specific embodiments, the arrays of integrated analytical devices further comprise an etch hardmask disposed between the high n material and the upper cladding of low n material.

In some embodiments, the collection module layer of the instant arrays of integrated analytical devices comprises a Fresnel lens structure. In specific embodiments, the Fresnel lens structure is a phase Fresnel zone plate.

In preferred embodiments of the instant arrays, at least one nanometer-scale aperture comprises a fluid sample that comprises a fluorescent species. In even more preferred embodiments, the fluorescent species is a fluorescently labeled nucleotide analog.

In specific embodiments, the plurality of nanometer-scale apertures comprise at least 100 nanometer-scale apertures. In other specific embodiments, the plurality of nanometer-scale apertures have a density of at least 1000 apertures per $cm^2$.

In another aspect, the invention provides methods for producing an array of integrated analytical devices comprising:

providing a substrate layer;
depositing a filter module layer on the substrate layer;
depositing a collection module layer on the filter module layer;
patterning and etching the filter module layer and the collection module layer to form an array of protrusions having tops and sides and having gaps between the protrusions;
depositing a reflective material on the array of protrusions such that the tops and sides of the protrusions comprise a reflective layer;

depositing a fill material on the reflective layer such that the fill material fills the gaps between the protrusions;

patterning and etching the fill material and reflective layer to remove the reflective layer from the tops of the protrusions;

depositing a first layer of low n material on the etched fill material and the tops of the protrusions;

depositing a high n material on the first layer of low n material;

depositing a second layer of low n material on the high n material to form an upper cladding and to complete a waveguide module layer disposed on the collection module layer;

depositing a zero-mode waveguide material on the surface of the waveguide module layer to form a zero-mode waveguide module layer;

patterning and etching the zero-mode waveguide module layer to define a plurality of nanometer-scale apertures penetrating into the upper cladding of the waveguide module layer.

In specific embodiments, the methods further comprise the step of patterning and etching the high n material to define a waveguide.

In other specific embodiments, the substrate layer is a detector layer.

In more specific embodiments, the substrate layer is a CMOS wafer.

In certain embodiments, the filter module layer comprises a dielectric filter.

In other embodiments, the filter module layer comprises an absorptive filter.

In specific embodiments, the substrate layer comprises a color-separation layer.

According to some embodiments, the step of etching the zero-mode waveguide module layer is stopped using an endpoint signal, and in some embodiments the zero-mode waveguide module layer is etched until at least one nanometer-scale aperture fully penetrates the upper cladding of the waveguide module layer.

In some embodiments, the methods further comprise the step of partially backfilling at least one nanometer-scale aperture, where, in some embodiments, the step of partially backfilling the at least one nanometer-scale aperture uses atomic layer deposition or low pressure chemical vapor deposition.

In some embodiments, the methods further comprise the step depositing an etch hardmask on the high n material prior to forming the upper cladding and completing the waveguide module layer.

In some embodiments, the second layer of low n material is $SiO_2$, and in some embodiments, the high n material is $Si_3N_4$.

In specific embodiments, the plurality of nanometer-scale apertures comprise at least 100 nanometer-scale apertures, and in other specific embodiments, the plurality of nanometer-scale apertures have a density of at least 1000 apertures per $cm^2$.

In yet another aspect, the invention provides methods for producing an array of integrated analytical devices comprising:

providing a substrate layer;

depositing a filter module layer on the substrate layer;

depositing a collection module layer on the filter module layer, wherein the collection module layer comprises a Fresnel lens;

depositing a first layer of low n material on the collection module layer;

depositing a high n material on the first layer of low n material;

depositing a second layer of low n material on the high n material to form an upper cladding and to complete a waveguide module layer;

depositing a zero-mode waveguide material on the surface of the waveguide module layer to form a zero-mode waveguide module layer;

patterning and etching the zero-mode waveguide module layer to define a plurality of nanometer-scale apertures penetrating into the upper cladding of the waveguide module layer.

In specific embodiments, the methods comprise the step of patterning and etching the high n material to define a waveguide.

In other specific embodiments, the substrate layer is a detector layer.

In still other specific embodiments, the substrate layer is a CMOS wafer.

In some embodiments, the filter module layer comprises a dielectric filter.

In some embodiments, the filter module layer comprises an absorptive filter.

In specific embodiments, the detector layer comprises a color-separation layer.

According to some embodiments, etching of the zero-mode waveguide module layer is stopped using an endpoint signal.

In specific embodiments, the zero-mode waveguide module layer is etched until at least one nanometer-scale aperture fully penetrates the upper cladding of the waveguide module layer.

In some embodiments, the methods further comprise the step of partially backfilling at least one nanometer-scale aperture.

In specific embodiments, the step of partially backfilling the at least one nanometer-scale aperture uses atomic layer deposition or low pressure chemical vapor deposition.

In some embodiments, the methods further comprise the step of depositing an etch hardmask on the high n material prior to forming the upper cladding and completing the waveguide module layer. In some specific embodiments, the second layer of low n material is $SiO_2$, and in some specific embodiments, the high n material is $Si_3N_4$.

In specific embodiments, the plurality of nanometer-scale apertures comprise at least 100 nanometer-scale apertures, and in other specific embodiments, the plurality of nanometer-scale apertures have a density of at least 1000 apertures per $cm^2$.

BRIEF DESCRIPTION OF THE DRAWINGS

FIGS. 18A and 18B illustrate an exemplary process flow for the manufacture of an array of integrated analytical devices comprising a dielectric filter module.

FIGS. 19A and 19B illustrate an exemplary process flow for the manufacture of an array of integrated analytical devices comprising an absorptive filter module.

FIG. 20 illustrates an exemplary process flow variant for the manufacture of an array of integrated analytical devices comprising a 2-color separation filter in the detector layer.

DETAILED DESCRIPTION OF THE INVENTION

Integrated Analytical Devices

Figure 1A:
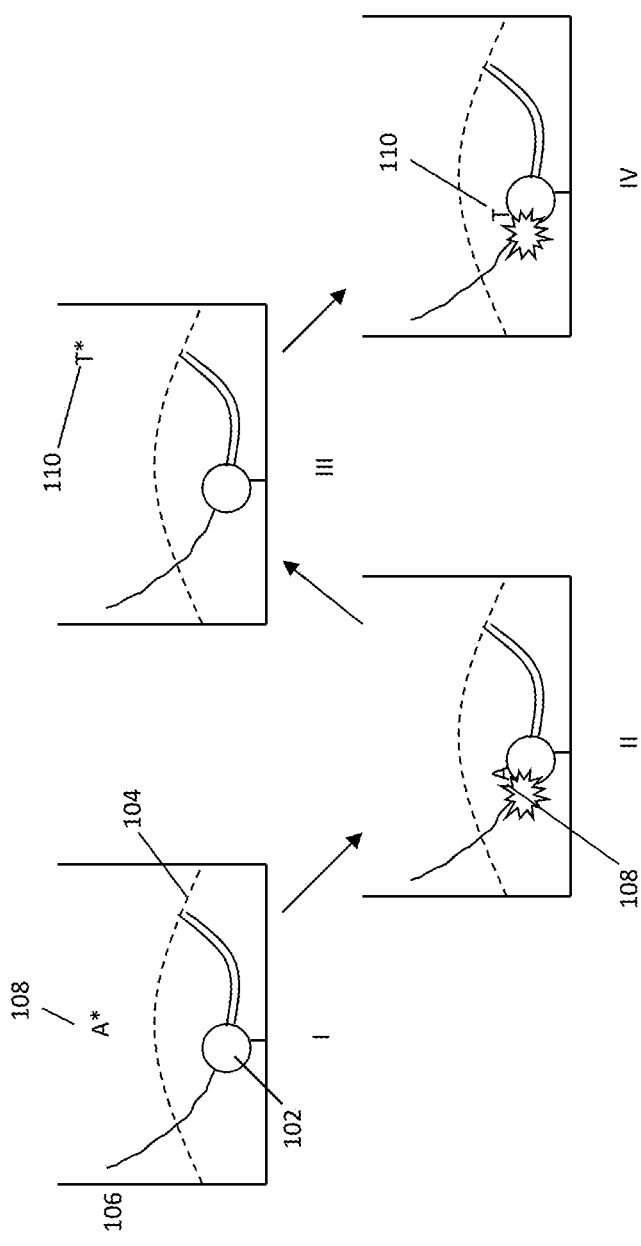
FIGS. 1A-B schematically illustrates an exemplary nucleic acid sequencing process that can be carried out using aspects of the invention.

Multiplexed optical analytical systems are used in a wide variety of different applications. Such applications can include the analysis of single molecules, and can involve observing, for example, single biomolecules in real time as they carry out reactions. For ease of discussion, such multiplexed systems are discussed herein in terms of a preferred application: the analysis of nucleic acid sequence information, and particularly, single molecule nucleic acid sequence analysis. Although described in terms of a particular application, it should be appreciated that the applications for the devices and systems described herein are of broader application.

In the context of single molecule nucleic acid sequencing analyses, a single immobilized nucleic acid synthesis complex, comprising a polymerase enzyme, a template nucleic acid, whose sequence one is attempting to elucidate, and a primer sequence that is complementary to a portion of the template sequence, is observed to identify individual nucleotides as they are incorporated into the extended primer sequence. Incorporation is typically monitored by observing an optically detectable label on the nucleotide, prior to, during or following its incorporation. In some cases, such single molecule analyses employ a "one base at a time approach", whereby a single type of labeled nucleotide is introduced to and contacted with the complex at a time. Upon incorporation, unincorporated nucleotides are washed away from the complex, and the labeled incorporated nucleotides are detected as a part of the immobilized complex.

In some instances, only a single type of nucleotide is added to detect incorporation. These methods then require a cycling through of the various different types of nucleotides (e.g., A, T, G and C) to be able to determine the sequence of the template. Because only a single type nucleotide is contacted with the complex at any given time, any incorporation event is by definition, an incorporation of the contacted nucleotide. These methods, while somewhat effective, generally suffer from difficulties when the template sequence includes multiple repeated nucleotides, as multiple bases may be incorporated that are indistinguishable from a single incorporation event. In some cases, proposed solutions to this issue include adjusting the concentrations of nucleotides present to ensure that single incorporation events are kinetically favored.

In other cases, multiple types of nucleotides are added simultaneously, but the nucleotides are distinguishable by the presence on each type of nucleotide of a different optical label. Accordingly, such methods can use a single step to identify a given base in the sequence. In particular, all four nucleotides, each bearing a distinguishable label, is added to the immobilized complex. The complex is then interrogated to identify which type of base was incorporated, and as such, the next base in the template sequence.

In some cases, these methods only monitor the addition of one base at a time, and as such, they (and in some cases, the single nucleotide contact methods) require additional controls to avoid multiple bases being added in any given step, and thus being missed by the detection system. Typically, such methods employ terminator groups on the nucleotide that prevent further extension of the primer once one nucleotide has been incorporated. These terminator groups are typically removable, allowing the controlled re-extension after a detected incorporation event. Likewise, in order to avoid confounding labels from previously incorporated nucleotides, the labeling groups on these nucleotides are typically configured to be removable or otherwise inactivatable.

In another process, single molecule primer extension reactions are monitored in real-time, to identify the continued incorporation of nucleotides in the extension product to elucidate the underlying template sequence. In such single molecule real time (or SMRT®) sequencing, the process of incorporation of nucleotides in a polymerase-mediated template dependent primer extension reaction is monitored as it occurs. In preferred aspects, the template/polymerase primer complex is provided, typically immobilized, within an optically confined region, such as a zero mode waveguide (ZMW), or proximal to the surface of a transparent substrate, optical waveguide, or the like (see e.g., U.S. Pat. Nos.

6,917,726, and 7,170,050 and U.S. Patent Application Publication No. 2007/0134128, the full disclosures of which are hereby incorporated by reference herein in their entirety for all purposes). The optically confined region is illuminated with an appropriate excitation radiation for the fluorescently labeled nucleotides that are to be used. Because the complex is within an optically confined region, or very small illumination volume, only the reaction volume immediately surrounding the complex is subjected to the excitation radiation. Accordingly, those fluorescently labeled nucleotides that are interacting with the complex, e.g., during an incorporation event, are present within the illumination volume for a sufficient time to identify them as having been incorporated.

Figure 1B:
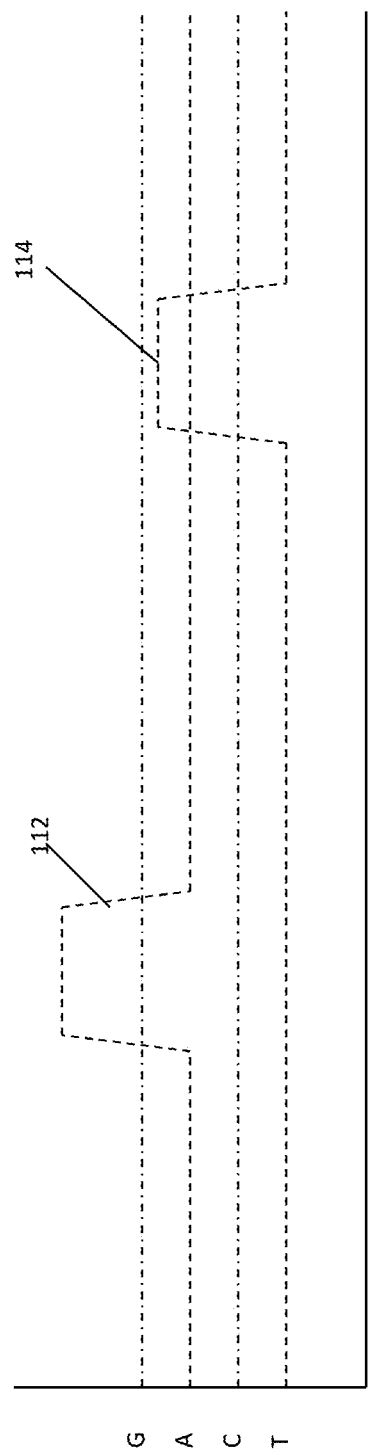

A schematic illustration of this sequencing process is shown in FIG. 1. As shown in FIG. 1A, an immobilized complex 102 of a polymerase enzyme, a template nucleic acid and a primer sequence are provided within an observation volume (as shown by dashed line 104) of an optical confinement, of e.g., a zero mode waveguide 106. As an appropriate nucleotide analog, e.g., nucleotide 108, is incorporated into the nascent nucleic acid strand, it is illuminated for an extended period of time corresponding to the retention time of the labeled nucleotide analog within the observation volume during incorporation which produces a signal associated with that retention, e.g., signal pulse 112 as shown by the A trace in FIG. 1B. Once incorporated, the label that attached to the polyphosphate component of the labeled nucleotide analog, is released. When the next appropriate nucleotide analog, e.g., nucleotide 110, is contacted with the complex, it too is incorporated, giving rise to a corresponding signal 114 in the T trace of FIG. 1B. By monitoring the incorporation of bases into the nascent strand, as dictated by the underlying complementarity of the template sequence, long stretches of sequence information of the template can be obtained.

Figure 2:
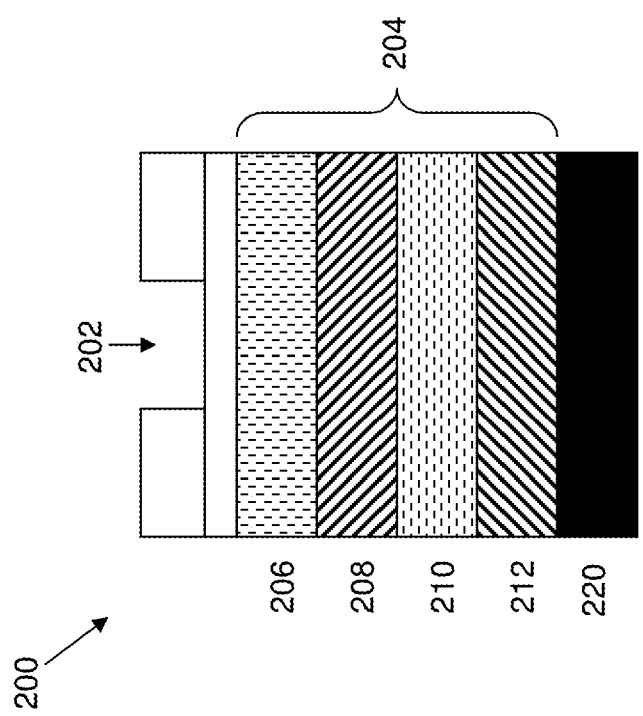
FIG. 2 provides a schematic block diagram of an integrated analytical device.

The above sequencing reaction may be incorporated into a device, typically an integrated analytical device, that provides for the simultaneous observation of multiple sequencing reactions, ideally in real time. While the components of each device and the configuration of the devices in the system may vary, each integrated analytical device typically comprises, at least in part, the general structure shown as a block diagram in FIG. 2. As shown, an integrated analytical device 200 typically includes a reaction cell 202, in which the reactants are disposed and from which the optical signals emanate. The analysis system further includes a detector element 220, which is disposed in optical communication with the reaction cell 202. Optical communication between the reaction cell 202 and the detector element 220 may be provided by an optical train 204 comprised of one or more optical elements generally designated 206, 208, 210 and 212 for efficiently directing the signal from the reaction cell 202 to the detector 220. These optical elements may generally comprise any number of elements, such as lenses, filters, gratings, mirrors, prisms, refractive material, or the like, or various combinations of these, depending upon the specifics of the application. By integrating these elements into a single device architecture, the efficiency of the optical coupling between the reaction cell and the detector is improved. Examples of integrated analytical systems, including various approaches for illuminating the reaction cell and detecting optical signals emitted from the reaction cell, are described in U.S. Patent Application Publication Nos. 2012/0014837, 2012/0019828, and 2012/0021525, which are each incorporated by reference herein in their entireties for all purposes.

Conventional analytical systems typically measure multiple spectrally distinct signals or signal events and must therefore utilize complex optical systems to separate and distinctly detect those different signal events. The optical path of an integrated device may be simplified, however, by a reduction in the amount or number of spectrally distinguishable signals that are detected. Such a reduction is ideally effected, however, without reducing the number of distinct reaction events that can be detected. For example, in an analytical system that distinguishes four different reactions based upon four different detectable signal events, where a typical system would assign a different signal spectrum to each different reaction, and thereby detect and distinguish each signal event, in an alternative approach, four different signal events would be represented at fewer than four different signal spectra, and would, instead, rely, at least in part, on other non-spectral distinctions between the signal events.

For example, a sequencing operation that would conventionally employ four spectrally distinguishable signals, e.g., a "four-color" sequencing system, in order to identify and characterize the incorporation of each of the four different nucleotides, would, in the context of an alternative configuration, employ a one-color or two-color analysis, e.g., relying upon a signals having only one or two distinct or distinguished spectral signals. However, in such an alternative configuration, this reduction in reliance on signal spectral complexity does not come at the expense of the ability to distinguish signals from multiple, i.e., a larger number of different signal producing reaction events. In particular, instead of relying solely on signal spectrum to distinguish reaction events, such an alternative configuration may rely upon one or more signal characteristics other than emission spectrum, including, for example, signal intensity, excitation spectrum, or both to distinguish signal events from each other.

In one particular alternative configuration, the optical paths in an integrated analytical device may thus be simplified by utilizing signal intensity as a distinguishing feature between two or more signal events. In its simplest iteration, and with reference to an exemplary sequencing process, two different types of nucleotides would bear fluorescent labels that each emit fluorescence under the same excitation illumination, i.e., having the same or substantially overlapping spectral band, and thus would provide benefits of being excited using a single excitation source and beam. The resulting signals from each fluorescent label would have distinct signal intensities or amplitudes under that same illumination, and would be distinguishable by their respective signal amplitudes. These two signals could have partially or entirely overlapping emission spectra, but separation of the signals based upon any difference in emission spectrum would be unnecessary.

Accordingly, for analytical systems using two or more signal events that differ in signal amplitude, the integrated analytical devices of such systems can readily benefit through the removal of some or all of those components that would normally be used to separate spectrally distinct signals, such as multiple excitation sources and their associated optical trains, as well as the color separation optics, e.g., filters and dichroics, for the signal events, which in many cases, requires at least partially separate optical trains and detectors for each spectrally distinct signal. As a result, the optical paths for these integrated analytical devices are greatly simplified, allowing placement of detector elements in closer proximity to reaction regions, and improving overall performance of the detection process for these devices.

Figure 3A:
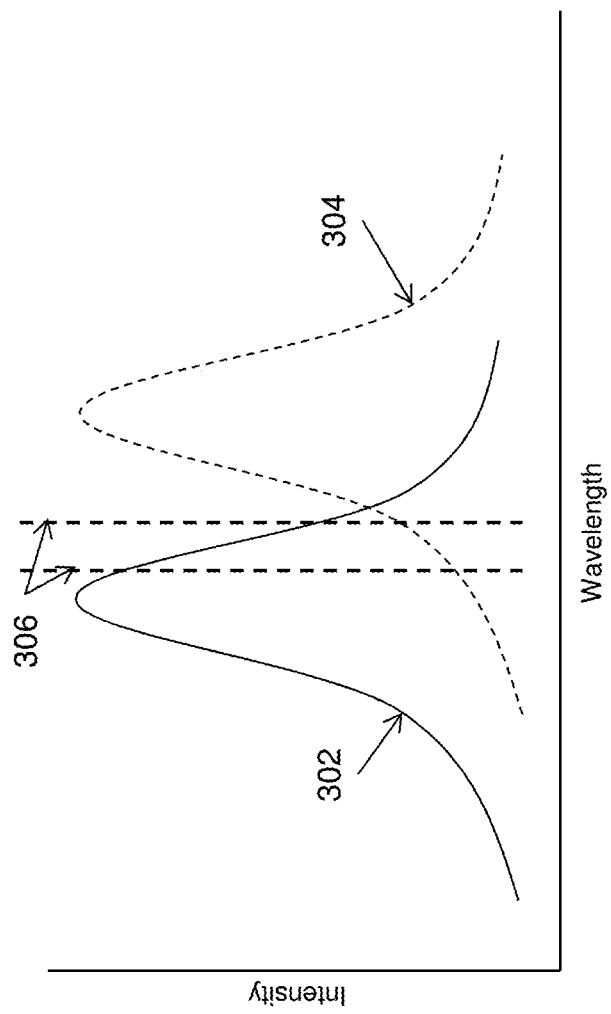
FIG. 3A provides a schematic of excitation spectra for two signal events and an indicated narrow band excitation illumination, while FIG. 3B schematically illustrates the resulting detected signal based upon the narrow band illumination of the two signal events.
Figure 3B:
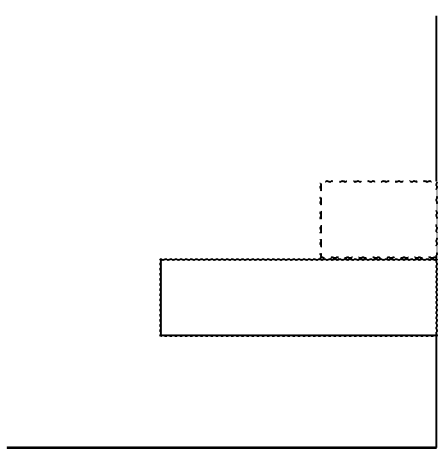

Provision of signal producing reactants that will produce different signal amplitudes under a particular excitation illumination profile may be accomplished in a number of ways. For example, different fluorescent labels may be used that present excitation spectral profiles that overlap but include different maxima. As such, excitation at a narrow wavelength will typically give rise to differing signal intensities for each fluorescent group. This is illustrated in FIG. 3A, which shows the excitation spectra of two different fluorescent label groups (solid and dashed lines 302 and 304, respectively). When subjected to excitation illumination at the wavelength range shown by vertical lines 306, each fluorescent label will emit a signal at the corresponding amplitude. The resulting signal intensities at a given excitation wavelength are then shown in the bar chart of FIG. 3B, shown as the solid lined and dashed lined bars, respectively. The difference in intensity of these two signal producing labels at the given excitation wavelength can then be readily used to distinguish the two signal events. As will be appreciated, such spectrally indistinct signals would not be easily distinguishable when occurring simultaneously, as they would result in an additive overlapping signal, unless, as discussed below, such spectrally indistinct signals result from spectrally distinct excitation wavelengths. As will be appreciated, this same approach may be used with more than two label groups where the resulting emission at a given excitation spectrum have distinguishable intensities or amplitudes.

Similarly, two different fluorescent labeling groups may have the same or substantially similar excitation spectra, but provide different and distinguishable signal emission intensities due to the quantum yield of those labeling groups.

Further, although described in terms of two distinct fluorescent dyes, it will be appreciated that each different labeling group may each include multiple labeling molecules. For example, each reactant may include an energy transfer dye pair that yields emissions of differing intensities upon excitation with a single illumination source. For example, a labeling group may include a donor fluorophore that is excited at a given excitation wavelength, and an acceptor fluorophore that is excited at the emission wavelength of the donor, resulting in energy transfer to the acceptor. By using different acceptors, whose excitation spectra overlap the emission spectrum of the donor to differing degrees, such an approach can produce overall labeling groups that emit at different signal amplitudes for a given excitation wavelength and level. Likewise, adjusting the energy transfer efficiency between the donor and acceptor will likewise result in differing signal intensities at a given excitation illumination.

Alternatively, different signal amplitudes may be provided by different multiples of signal producing label groups on a given reactant, e.g., putting a single label molecule on one reactant while putting 2, 3, 4 or more individual label molecules on a different reactant. The resulting emitted signal will be reflective of the number of labels present on a reactant and thus will be indicative of the identity of that reactant.

Exemplary compositions and methods relating to fluorescent reagents, such as nucleotide analogs, useful for the above purposes are described in, for example, U.S. Patent Application Publication Nos. 2012/0058473; 2012/0077189; 2012/0052506; 2012/0058469; 2012/0058482; 2010/0255488; 2009/0208957, which is each incorporated by reference herein in its entirety for all purposes.

As described above, integrated analytical devices making use of such approaches see a reduction in complexity by elimination of spectral discrimination requirements, e.g., using signal amplitude or other non-spectral characteristics as a basis for signal discrimination. Integrated analytical devices that combine such non-spectral discrimination approaches with the more common spectral discrimination approaches may also provide advantages over more complex spectral discrimination systems. By shifting from a "four-color" discrimination system to a system that distinguishes signals based upon signal intensity and color, one can still reduce the complexity of the overall optical system relative to a conventional four-color separation scheme. For example, in an analytical operation that detects four discrete reaction events, e.g., in a nucleic acid sequencing analysis, two signal events may be provided within a given emission/detection spectrum, i.e., emitting signals within the same spectral window, and the other two events within a distinct emission/detection spectrum. Within each spectral window, the pair of signal events produce distinguishable signal intensities relative to each other.

For ease of discussion, this concept is described in terms of two groups of fluorescent signal events, where members of each group differ by fluorescent intensity, and the groups differ by virtue of their emission spectrum. As will be appreciated, the use of simplified optics systems, e.g., using two detection channels for two distinct emission spectra, does not require that the emission profiles of the two groups of signals do not overlap or that the emission spectra of members of each group perfectly overlap. Instead, in many preferred aspects, more complex signal profiles may be used where each different signal event possesses a unique emission spectrum, but in a way that each signal will present a signal profile within the two detection channels that is unique, based upon the signal intensity in each channel.

Figure 4:
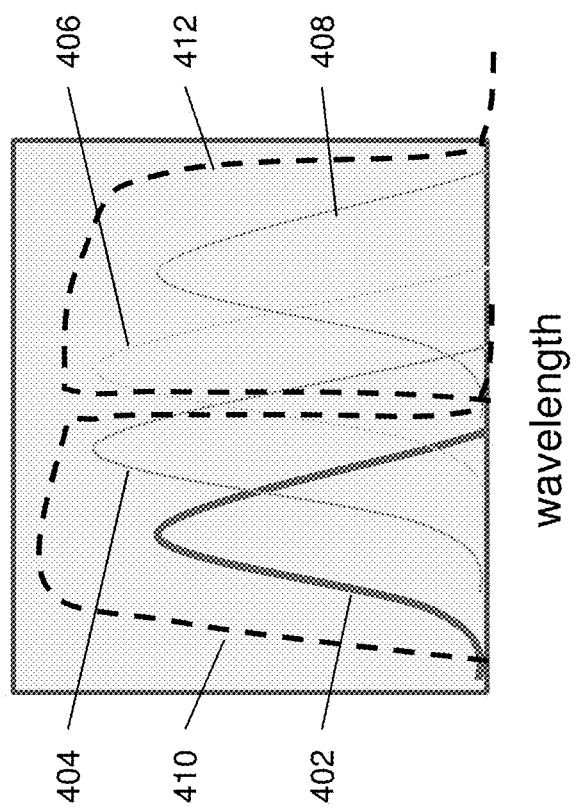
FIG. 4 schematically illustrates the signal profiles for each of four fluorescent labeling groups, overlain with each of two different filter profiles.

FIG. 4 schematically illustrates the signal profiles for each of four fluorescent labeling groups, overlain with each of two different filter profiles. As shown, four label groups yield emission spectra 402, 404, 406 and 408, respectively. While the signals from these four groups partially overlap each other, they each have different maxima. When subjected to a two channel filter scheme, as shown by pass filter lines 410 and 412, the signal from each label will produce a unique signal profile between the two detection channels. In particular, signals are routed through an optical train that includes two paths that are filtered according to the spectral profile shown. For each signal, different levels of emitted light will pass through each path and be detected upon an associated detector. The amount of signal that passes through each filter path is dictated by the spectral characteristics of the signal.

Figure 5:
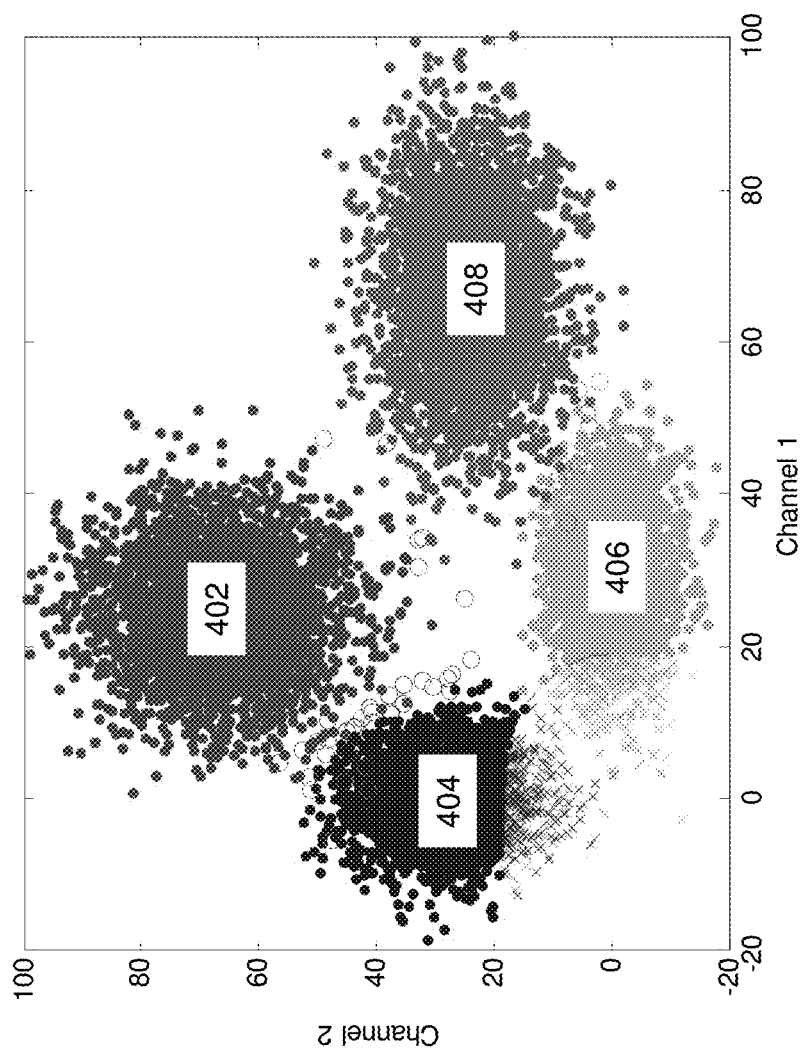
FIG. 5 illustrates modeled signal data plotted as a function of detected channel 1 and channel 2 intensity.

FIG. 5 illustrates modeled signal data plotted as a function of detected channel 1 and channel 2 intensity. As can be seen, signals 402, 404, 406 and 408 associated with each different group presents a unique signal profile that is a combination of channels 1 and 2 intensity. In particularly preferred aspects, each of the label groups or signal-producing reactants that is sought to be distinguished using the schemes described herein, is selected to be sufficiently different from each other label in at least one of the two detection channels so as to be distinguishable from each other signal based upon a combination of signals from each of the two detection channels.

In the case of the above described mixed-mode schemes, detection systems may be provided that include at least two distinct detection channels, where each detection channel passes light within a spectrum that is different from each other channel. Such systems also include a reaction mixture within optical communication of the detection channels, where the reaction mixture produces at least three different optical signals that each produces a unique signal pattern within the two detection channels, as compared to the other optical signals.

In each case, each signal-producing reactant is selected to provide a signal that is entirely distinct from each other signal in at least one of signal intensity and signal channel. As noted above, signal intensity in a given channel is dictated, in part, by the nature of the optical signal, e.g., its emission spectrum, as well as the filters through which that signal is passed, e.g., the portion of that spectrum that is allowed to reach the detector in a given channel. However, signal intensity can also be modulated by random variables, such as orientation of a label group when it is emitting signal, or other variables of the particular reaction. Accordingly, for a signal's intensity to be assured of being entirely different from the intensity of another signal within a given channel, in preferred aspects, this variation is accounted for.

Figure 6:
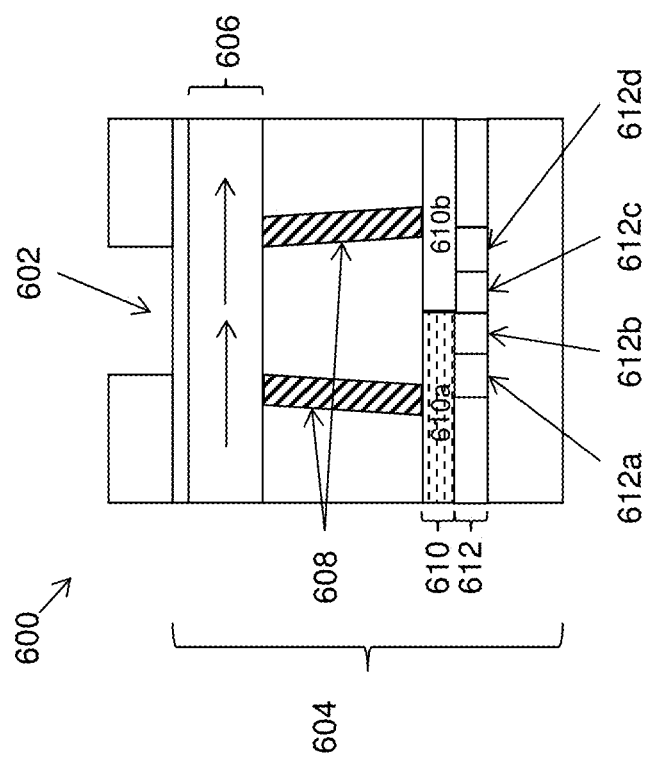
FIG. 6 schematically illustrates an integrated analytical device for detecting signals as shown in FIG. 5.

With a reduced number of spectrally distinct signal events, the complexity of the optical paths for the integrated devices is also reduced. FIG. 6 illustrates a not-to-scale example device architecture for performing optical analyses, e.g., nucleic acid sequencing processes, that rely in part on non-spectral discrimination of differing signals, and optionally, in part on spectral distinction. As shown, an integrated analytical device 600 includes a reaction region 602 that is defined upon the surface layer of the device. As shown, the reaction region comprises a nanowell disposed in the surface layer. Such nanowells may constitute depressions in a substrate surface or apertures disposed through additional substrate layers to an underlying transparent substrate, e.g., as used in zero mode waveguide arrays (See, e.g., U.S. Pat. Nos. 7,181,122 and 7,907,800).

Excitation illumination is delivered to the reaction region from an excitation light source (not shown) that may be separate from or also integrated into the substrate. As shown, an optical waveguide (or waveguide layer) 606 may be used to convey excitation light (shown by arrows) to the reaction region/nanowell 602, where the evanescent field emanating from the waveguide 606 illuminates reactants within the reaction region 602. Use of optical waveguides to illuminate reaction regions is described in e.g., U.S. Pat. No. 7,820,983 and U.S. Patent Application Publication No. 2012/0085894, which are each incorporated by reference herein in their entireties for all purposes. The nanowell acts to enhance the emission of fluorescence downward into the device and limit the amount of light scattered upwards.

The emitted light is directed into the device through an integrated optical train 604 comprising one or more optical elements. The optical train optionally includes light channeling components 608 to efficiently direct emitted light from the reaction regions to a detector layer 612 disposed beneath the reaction region. As described in more detail below, the collection path may include reflective cones and/or optical lenses to channel the emitted light and/or to split the light into multiple beams. The optical lenses within the collection path may be refractive lenses but are preferably diffractive lenses. The lenses may, for example, split the emitted light into two, three, four, or even more beams directed onto the detector layer. The split beams may be organized in a linear fashion, or they may be arranged in an array, for example in a 2×2 beam array or the like, depending on the configuration of the detector elements.

The detector layer typically comprises one, or preferably multiple, detector elements 612a-d, e.g., pixels in an array detector, that are optically coupled to a given reaction region. Although illustrated as a linear arrangement of pixels 612a-d, it will be appreciated that such pixels may be arranged in a grid, n×n square, n×m rectangle, annular array, or any other convenient orientation.

Emitted signals from the reaction region 602 that impinge on these pixels are then detected and recorded. As noted above, an optional single filter layer 610 is disposed between the detector layer and the reaction region, to permit different spectrally distinct signals to travel to different associated pixels 612a and 612b in the detector layer 612. For example, the portion 610a of filter layer 610 allows signals having a first emission spectrum to reach its associated pixels 612a and 612b, while filter portion 610b of filter layer 610 allows only signals having a distinct second spectrum to reach its associated pixels 612c and 612d.

In the context of a sequencing system exploiting such a configuration, incorporation of two of the four nucleotides would produce signals that would be passed through filter portion 610a to pixels 612a and 612b, and blocked by filter portion 610b. As between these two signals, one signal would have a signal intensity higher than the other such that the pixels 612a and 612b in detector layer 612 would be able to produce signal responses indicative of such differing signal intensities. Likewise, incorporation of the other two nucleotides would produce signals that would be passed through filter portion 610b to its associated pixels 612c and 612d, while filter portion 610a would block those signals from reaching pixels 610a and 610b. Again, the signals associated with these two latter signal events would differ based upon their signal intensities or amplitudes. In some configurations, for example if the amplitudes of the different dyes are properly calibrated, it may alternatively be possible to differentiate four different dyes using only two pixels in the detector layer.

The detector layer is then operably coupled to an appropriate circuitry, typically integrated into the substrate, for providing a signal response to a processor that is optionally included integrated within the same device structure or is separate from but electronically coupled to the detector layer and associated circuitry. Examples of types of circuitry are described in U.S. Patent Application Publication No. 2012/0019828.

As will be appreciated from the foregoing disclosure and FIG. 6, the integrated analytical devices described herein do not require the more complicated optical paths that are necessary in systems utilizing conventional four-color optics, obviating the need for excessive signal separation optics, dichroics, prisms, or filter layers. In particular, although shown with a single filter layer, as noted, in optional aspects, the filter layer could be eliminated or could be replaced with a filter layer that blocks stray light from the excitation source rather than distinguishing different emission signals from the reaction region. Even including the filter layer 610, results in simplified and/or more efficient optics as compared to conventional four-color systems, which would require either multilayer filters, or narrow band pass filters, which typically require hybrid layers or composite approaches over each subset of pixels, thus blocking signal from reaching three of the four pixel subsets at any given emission wavelength, resulting in detection of far fewer photons from each signal event. The optics configuration shown in FIG. 6, on the other hand, only blocks a smaller portion of the overall signal light from reaching the detector. Alternatively, such conventional systems would require separation and differential direction of all four different signal types, resulting in inclusion of additional optical elements, e.g., prisms or gratings, to achieve spectral separation.

Figure 7:
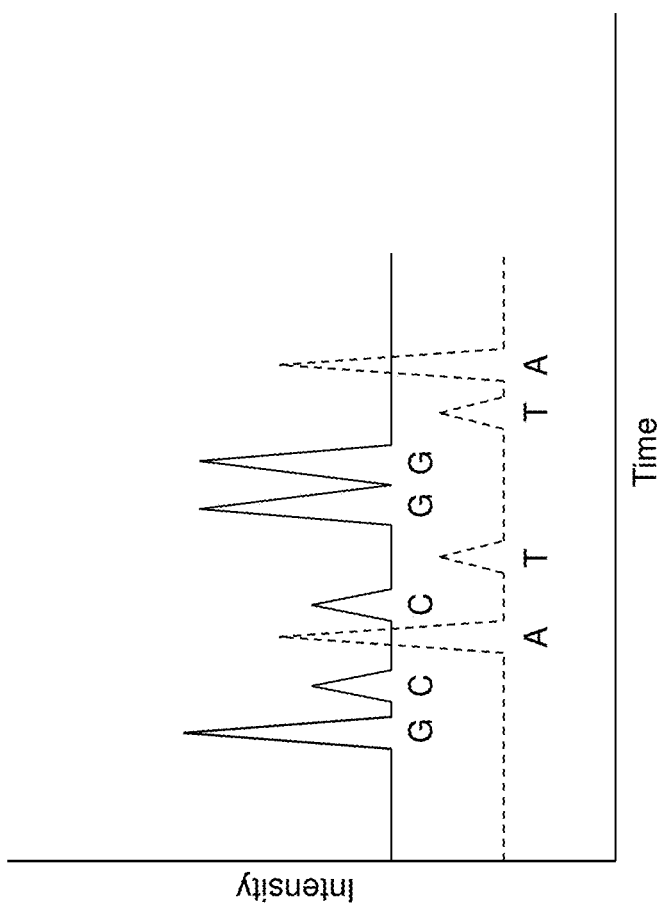
FIG. 7 schematically illustrates signal traces for a two-color, two-amplitude sequence-by-synthesis reaction.

FIG. 7 shows a schematic exemplar signal output for a real time sequencing operation using a two color/two amplitude signal set from an integrated system of the invention where one trace (dashed) denotes signals associated with incorporation of A (high intensity signal) and T (lower intensity signal) bases, while the other signal trace (solid line), denotes the signals of a different emission spectrum, associated with G (high) and C (low) bases. The timing of incorporation and the identity of the base incorporated, as derived from the color channel and intensity of the signal, are then used to interpret the base sequence.

The process flows disclosed as part of the instant invention provide for the production of novel filter architectures. In particular, as noted above, typical four-color detection schemes operate through the detection of signal at a narrow spectral band corresponding to and correlating with an emission signal maximum emitted from a particular reaction event, e.g., incorporation of a single type of nucleotide in a sequencing operation, with the remainder of the spectrum being blocked and disregarded. In the context of single molecule analyses and/or small scale integrated devices, however, where signal detection efficiency is of far greater importance, discarding of any photons associated with a particular reaction event should be avoided as much as possible.

Accordingly, in certain aspects, the present invention provides arrays of integrated analytical devices for use in optical detection systems that reduce the attenuation of optical signals emanating from the reaction region and ultimately, that reach the detector. This permits detection and signal discrimination that is based upon a greater amount of emitted and detected signal.

One approach to this aspect of such optical detection systems is ideally illustrated in the context of multicolor fluorescence detection systems, e.g., the four-color fluorescence systems described above. As noted, typically, such systems include reactions that produce different optical signals based upon the occurrence of different reaction events, such as incorporation of different fluorescently labeled nucleotides in many nucleic acid "sequencing by synthesis" applications.

Signals that are indicative of the addition of a given base to the polymerase/template/primer replication complex are typically passed through a series of optical filters that narrowly separate out each signal component based upon its spectral maximum, and direct that separated component to a separate detector or sensing region of a detector, e.g., a pixel or subset of pixels in an array detector. The type of base added in a given step is then identified from the narrow signal component that is detected at that particular juncture in the assay. While this method is highly effective for many applications, where signal is very limited, e.g., where attempting to detect signal from a very small reaction volume or a single molecule of a fluorescent label, narrowly attenuating that signal becomes more problematic.

Figure 8A:
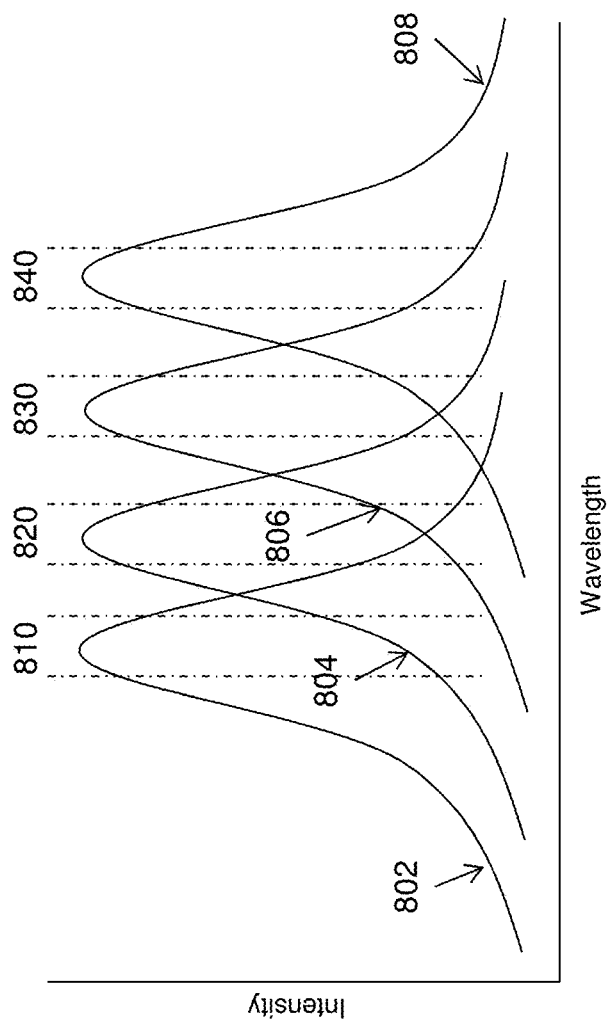
FIG. 8A schematically illustrates emission spectra of four distinct signal events, e.g., fluorescently labeled nucleotide analogs.
Figure 8B:
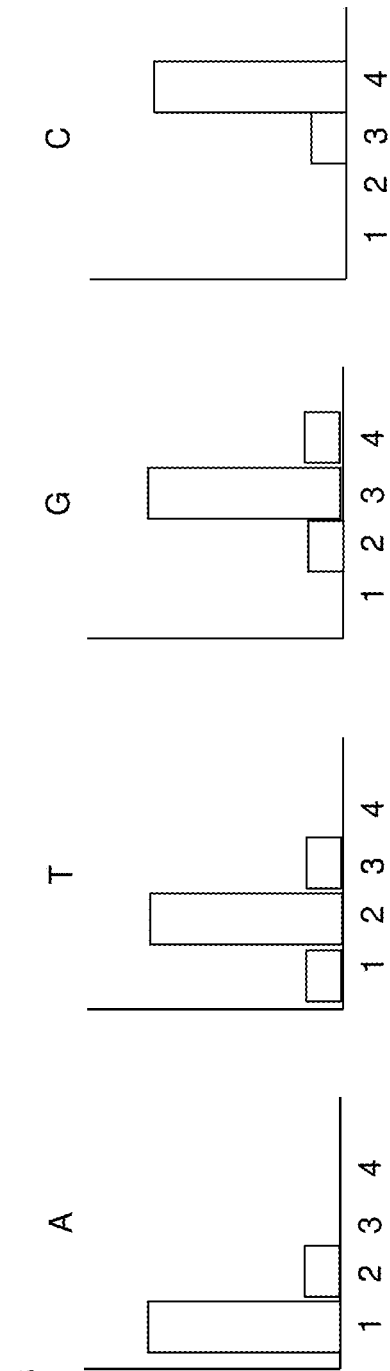
FIG. 8B schematically illustrates a signal profile at each detector element based upon a typical four-color separation scheme.

The potential difficulties are schematically illustrated in FIG. 8 with reference to an exemplary four-color DNA sequencing system. As shown in FIG. 8A, the signal palette for the four bases in an exemplary DNA sequencing reaction are shown as four distinct, albeit partially overlapping emission maxima 802, 804, 806 and 808. In conventional four-color detection systems, signals from the reaction zone are passed through a filter system, typically comprised of multiple filters, that allow a narrow spectral band, e.g., spectral band 810, 820, 830 or 840, that corresponds to an emission maximum for each differently labeled nucleotide (e.g., A, T, G, and C, respectively) to reach one of four different detectors or detection zones on the same detector. For convenience, different detectors or different detection zones on the same detector are interchangeably referred to herein as different "detectors". FIG. 8B shows a schematic illustration of a signal profile for each base, based upon such conventional systems. As shown, e.g., for an A base incorporation, a signal for a given base is substantially only detected upon detector 1, while being blocked from or significantly attenuated at detectors 2, 3 and 4.

This technique is effective where signals of a given spectral band are completely separated from other signals and the separated signals are directed to a detector where all light associated with that signal can be detected. However, for miniaturized systems, the ability to completely separate different signals and detect all light associated with the separated components is impaired by the structural size of the devices. In particular, signal "separation" in certain implementations of integrated analytical devices may fractionate a signal and subject each fraction to a different filter set, in order to distinguish different signals.

In accordance with an improved alternative integrated device architecture, however, the filtering approach is inverted such that each filter for each of the different detectors or sensing elements would represent a narrow-band blocking filter disposed between the assay region and the detector, that only blocks the indicated portion of the spectrum, e.g., spectral band 1, 2, 3 and 4 in FIG. 8A, from reaching its respective detector component. Accordingly, each signal results in detection at three of the four detection zones.

Figure 9:
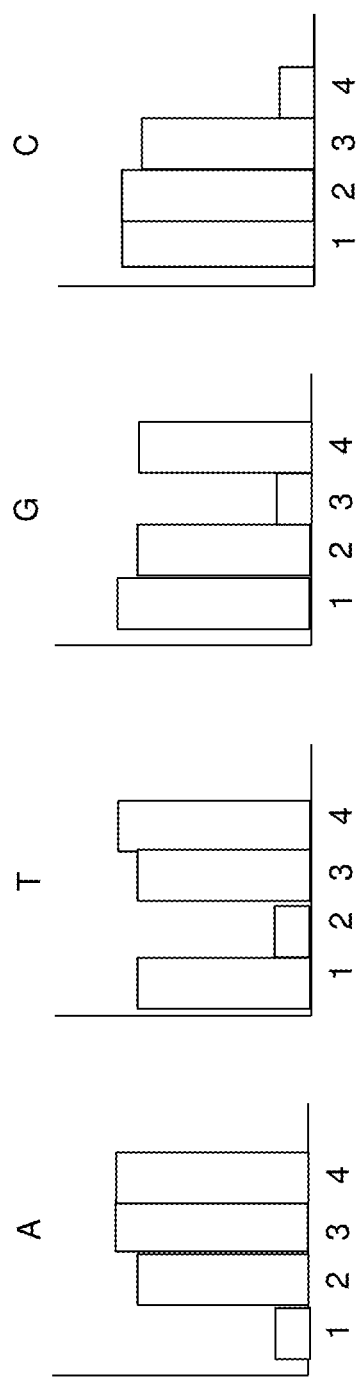
FIG. 9 schematically illustrates a similar signal profile at each of four detector elements, but based upon an alternative filter architecture.

FIG. 9 schematically shows the signal profile at each of the detectors for all four bases. As can be seen, each signal is detected from photons reaching three of the four detectors and that are only attenuated at a single different detector by virtue of the narrow band blocking filter. As is also apparent, each signal event results in a greater amount of detected signal than would be provided in a signal profile from a narrow-band pass filter architecture, e.g., as illustrated in FIG. 8B, above. The resulting unique signal profile over multiple detectors can then be used to identify the nature of the fluorescent label, and consequently, the added base. In effect, such a filter scheme results in a "negative" of the signal profile from the conventional narrow band-pass scheme. Although described in terms of four-color schemes, it will be appreciated that this approach can also be applied to fewer or greater than four-color schemes, e.g., three-color schemes, five-color schemes, or the like.

Described differently, each detector or detector region, e.g., pixel subset on a given detector, has a filter layer that permits greater than 25% of light from the totality of the various different optical signals impinging upon the filter layer to pass through to the detector or pixel subset. In some configurations, that filter layer will permit greater than 50% of light from the totality of the various different optical signals impinging upon the filter layer to pass through the detector or pixel subset, and in additional configurations, greater than 60% of the light that impinges on the filter from the totality of optical signals will pass through a given filter layer to reach its associated pixel subset, and in some cases, greater than 70% of the light that impinges on the filter from the totality of optical signals will pass through a given filter layer to reach its associated pixel subset.

In addition to benefits of increased signal at each detector, this aspect of an improved alternative device architecture provides additional benefits in the context of integrated optical devices, e.g., devices in which at least the optical components, e.g., filters and the like, and detector elements are integrated into a single substrate. In particular, by providing a single narrow-band blocking filter type, rather than a filter stack between the assay location and a given detector, the overall architecture of the device can be greatly simplified. In particular, by using only a single narrow band blocking filter, it is possible to use single layers or single composition filter layers rather than hybrid filter layers or filter compositions.

Further, because fewer layers are provided between the assay region and the detector, the assay location can be provided in closer proximity to the detector, reducing the potential for signal loss, cross-talk, and other signal transmission difficulties that may be inherent in more complex optical trains. In particular, where a more conventional four-color system might require a four-layer optical filter at each detector, and result in a substantially attenuated signal, the systems described herein would include a single filter layer at each detector, and result in the higher level signal profiles described above.

The devices and systems disclosed herein may generally be characterized by virtue of the number of filter layers as it relates to the number of spectrally distinct optical signals to be detected.

In yet another alternative approach, the integrated analytical systems disclosed herein simplify the optical path by relying on assay processes that utilize other than spectral separation of different signals to distinguish different signal events. Examples of such temporal signal distinction are described in U.S. Patent Application Publication Nos. 2012/0019828 and 2009/0181396, incorporated by reference herein in their entireties for all purposes, and relies upon the use of different fluorescent labeling groups that possess distinct excitation spectra. By modulating the excitation light through each of the different excitation spectra, and correlating any resulting emitted fluorescence with the excitation spectrum at a given time, one can identify what excitation light caused a given emission, and consequently identify the fluorescent label and the reaction or reagent with which it is associated. As will be appreciated, this type of excitation and detection scheme requires no signal filtering optics, other than as necessary to screen out background or other incidental light, e.g., excitation illumination.

In the context of a number of aspects of the systems disclosed herein, for systems that have greater than 2, greater than 3 or greater than 4 or more, spectrally distinct optical signals, the system will include a filter component that rejects or attenuates fewer than n−1 of those distinct optical signals, where n is the number of spectrally distinct signals, e.g., signals associated with different fluorescent label sets or different labeled reactants or reaction products. For example, with reference to the scheme described for FIG. 6, above, a single signal attenuating filter, e.g., filter layer portion 610a in FIG. 6, may be used between the reaction region and a given detector, with a different single attenuating filter, e.g., filter layer portion 610b in FIG. 6, being provided over each of the four different detectors. Likewise, for a two-color, two signal intensity signal profile for a given analysis, again a single signal attenuating filter element is provided over two of the detectors and a different single signal attenuating filter is provided over the other two detectors.

Arrays of Integrated Analytical Devices

In order to obtain the volumes of sequence information that may be desired for the widespread application of genetic sequencing, e.g., in research and diagnostics, higher throughput systems are desired. By way of example, in order to enhance the sequencing throughput of the system, multiple complexes are typically monitored, where each complex is sequencing a separate template sequence. In the case of genomic sequencing or sequencing of other large DNA components, these templates will typically comprise overlapping fragments of the genomic DNA. By sequencing each fragment, one can then assemble a contiguous sequence from the overlapping sequence data from the fragments.

As described above, and as shown in FIG. 1, the template/DNA polymerase-primer complex of such a sequencing system is provided, typically immobilized, within an optically confined region, such as a zero mode waveguide (ZMW), or proximal to the surface of a transparent substrate, optical waveguide, or the like. Preferably, such reaction cells are arrayed in large numbers upon a substrate in order to achieve the scale necessary for genomic or other large-scale DNA sequencing approaches. Such arrays preferably comprise a complete integrated analytical device, such as, for example, the devices shown in the block diagrams of FIGS. 2 and 6. Examples of integrated systems comprising arrays of optical analytical devices are provided in U.S. Patent Application Publication Nos. 2012/0014837; 2012/0019828; and 2012/0021525.

Arrays of integrated analytical devices, such as arrays of devices comprising ZMWs, can be fabricated at ultra-high density, providing anywhere from 1000 ZMWs per $cm^2$, to 1,000,000 ZMWs per $cm^2$, or more. Thus, at any given time, it may be desirable to analyze the reactions occurring in from 100, 1000, 3000, 5000, 10,000, 20,000, 50,000, 100,000 or 1 Million, 10 Million or more ZMWs or other reaction regions within a single analytical system or even on a single substrate.

Using the foregoing systems, simultaneous targeted illumination of thousands or tens of thousands of ZMWs in an array has been described. However, as the desire for multiplex increases, the density of ZMWs on an array, and the ability to provide targeted illumination of such arrays, increases in difficulty, as issues of ZMW cross-talk (signals from neighboring ZMWs contaminating each other as they exit the array), decreased signal:noise ratios arising from higher levels of denser illumination, and the like, increase. The arrays and methods of the instant invention address some of these issues.

The position on the detector upon which a given signal is incident is indicative of (1) the originating ZMW in the array, and (2) the emission characteristics of the signal component, which is used, for example, to identify the type of fluorescently labeled nucleotide analog incorporated in an extension reaction. As noted above, the detector may include in some cases multiple sensing elements, each for detecting light having a different color spectrum. For example, in the case of sequencing, the sensor for each reaction cell may have 4 elements, one for each of the four bases. In some cases, the sensor elements provide color discrimination, in other cases, color filters are used to direct the appropriate color of light to the appropriate sensor element. In some cases, the sensor elements detect intensity of signal only, without discriminating color. In some cases, the sensor elements identify the incorporated nucleotide using a combination of emission characteristics.

Figure 10:
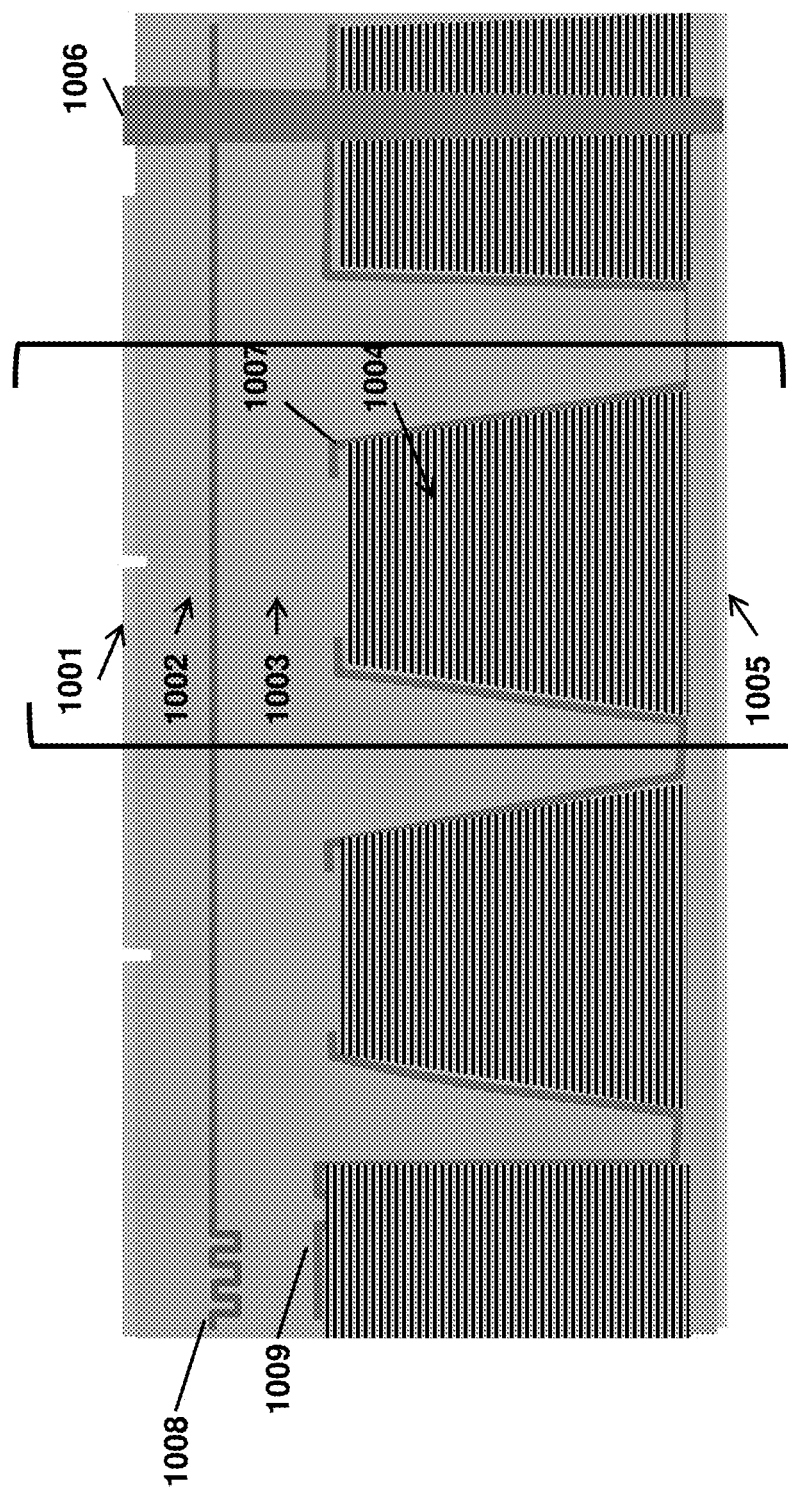
FIG. 10 schematically illustrates an exemplary array of integrated analytical devices, where each device comprises a dielectric filter layer within the reflective cone, and there is no color separation in the detector layer.
Figure 11:
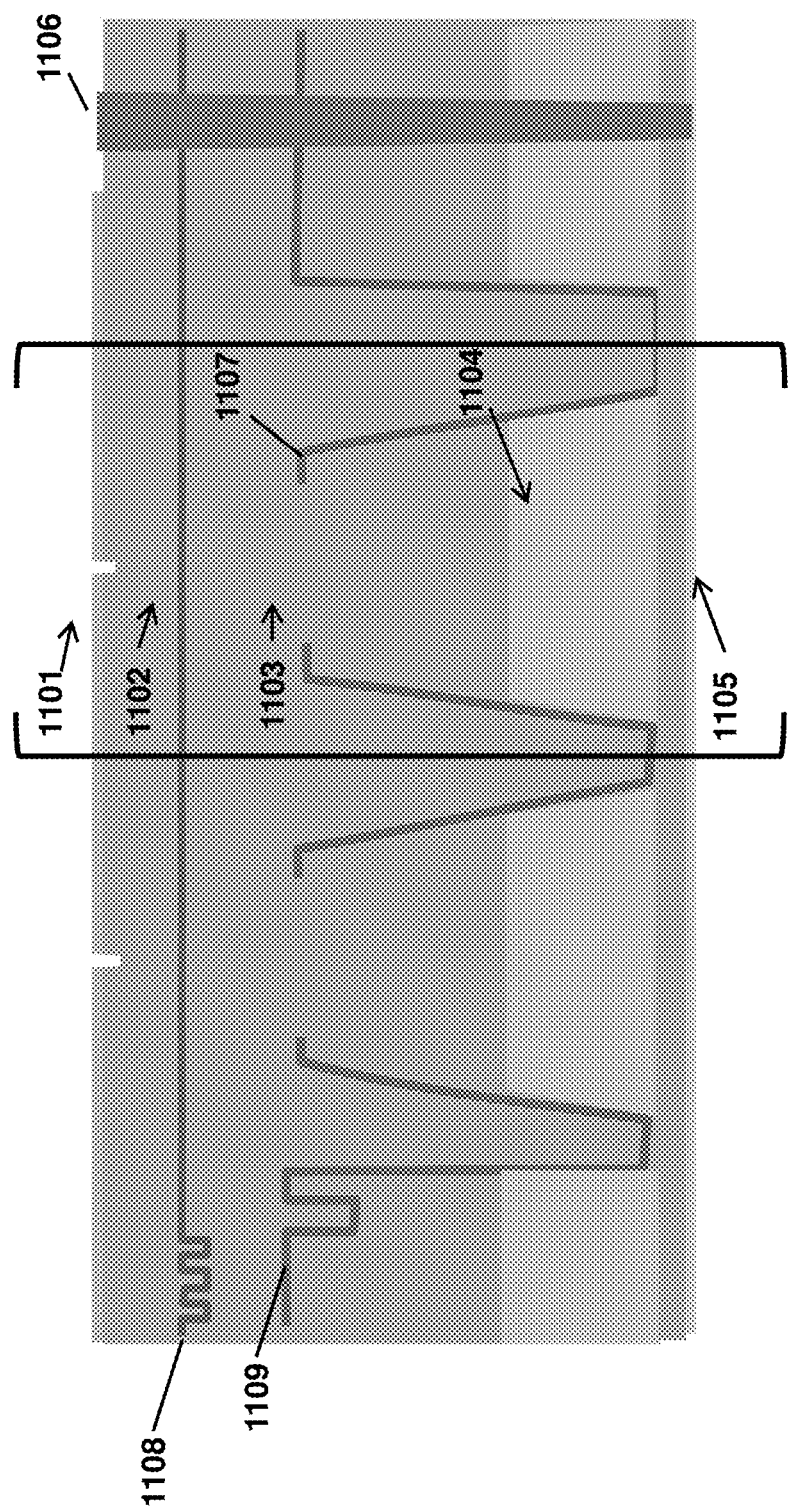
FIG. 11 schematically illustrates an exemplary array of integrated analytical devices, where each device comprises an absorptive filter layer within the reflective cone, and there is no color separation in the detector layer.
Figure 12:
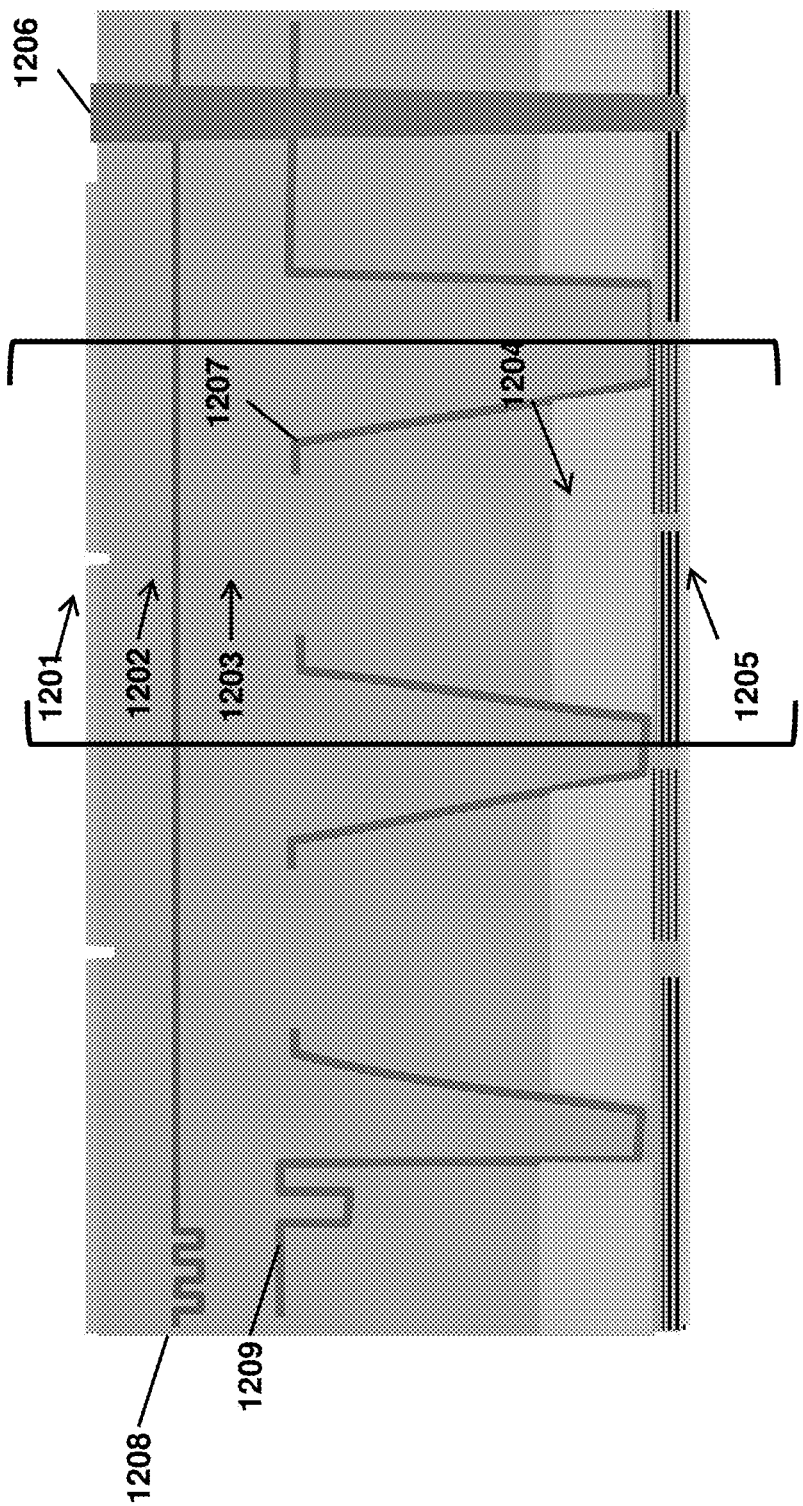
FIG. 12 schematically illustrates an exemplary array of integrated analytical devices, where each device comprises an absorptive filter layer within the reflective cone, and where the detector layer includes a two-color separation filter stack.

Exemplary arrays of integrated analytical devices are illustrated schematically in FIGS. 10-12, wherein the repeating device unit of each array is represented as the area within the brackets in each drawing. As would be understood by one of ordinary skill in the art, the arrays of the instant invention can include any desired number and density of ZMWs by repetition of the individual analytical device unit in two dimensions, i.e., along the horizontal axis of the drawing and along the axis extending perpendicular to the plane of the drawing. Such repetition of the individual analytical device unit allows the generation of two-dimensional arrays with extremely large numbers and ultra-high densities, as described above. Fabrication of such arrays is described in the following section using the methods of the instant disclosure. The arrangement and placement of individual analytical devices within the two-dimensional array is achieved through the fabrication methods and can be modified as desired within the scope of the instant invention. In some cases, the analytical devices are arranged relative to one another in regular rows and columns, but other arrangements may also be generated, if so desired, during the fabrication process.

The arrays of integrated analytical devices illustrated in FIGS. 10-12 share several common features. For example, each integrated analytical device within the array includes a ZMW module layer (1001, 1101, and 1201) comprising a nanometer-scale aperture penetrating into the upper cladding of the waveguide module layer (1002, 1102, and 1202). The waveguide module layer comprises a core of high refractive index ("high n") and a cladding of low refractive index ("low n") that encapsulates the core. Examples of waveguides useful in the waveguide module layers of the instant application are disclosed in U.S. Pat. No. 7,820,983 and U.S. Patent Application Publication No. 2012/0085894. As would be understood by one of ordinary skill in the art, the waveguide module layer may propagate excitation illumination to the ZMWs of the array in a specific pattern, for example through a series of channels within the waveguide module layer, or may propagate the illumination non-specifically in two dimensions, for example through a slab of core material that is defined within the cladding of the waveguide module layer.

The individual analytical devices within an array typically further include a collection module layer (1003, 1103, and 1203) and a filter module layer (1004, 1104, and 1204), which are disposed between the ZMW and the detector layer (1005, 1105, and 1205), just below the waveguide module layer. The collection module layer and the filter module layer are preferably fashioned in a cone shape that is defined by a reflective layer (1007, 1107, and 1207) covering the sides of the collection module layer and filter module layer but providing an opening for emitted light to pass from the ZMW to the detector.

The arrays of integrated analytical devices may optionally further include features on the periphery of the array, such as a deep trench (1006, 1106, 1206), an optical coupler (1008, 1108, and 1208), and an alignment feature (1009, 1109, 1209). These features are typically not repeated in each of the individual analytical device units but may be separately repeated as part of an array, for example in several locations on a wafer, if so desired. These features may, for example, facilitate the assembly of a completed array into a larger analytical device, or provide for a connection pathway between the top surface and the bottom surface of the array (e.g., the alignment feature and the deep trench) or may provide for a connection between a light source and the waveguide module layer (e.g., the optical coupler). As is understood in the art, proper alignment of the optical features within each integrated analytical device is critical in the effective function of an integrated analytical device. Alignment features, such as for example those just described, may be used to effect or facilitate such alignment. Other components may include packaging components, e.g., components that provide fluidic interfaces with the surface of the array, such as flow cells, wells or recesses, channel networks, or the like, as macrostructures as compared to the surface defined structures above, as well as alignment structures and casings that provide structural protection for the underlying arrays and interactive functionality between the arrays and instrument systems that work with/analyze the arrays. Other such optional features may be included in the arrays without deviating from the overall scope of the invention.

The arrays of integrated analytical devices illustrated in FIGS. 10-12 differ in the nature of their filter module layers and in the optional inclusion of a color-separation thin-film stack layer as part of the detector layer. Specifically, the filter module layer of the array illustrated in FIG. 10 comprises a dielectric filter layer within the reflective cone, whereas the filter module layer of the array illustrated in FIG. 11 comprises an absorptive filter layer within the reflective cone. Neither of these examples includes any color-separation layers. The devices of these arrays therefore correspond most similarly to the device of FIG. 6, with a single filter layer 610 (i.e., 610a and 610b are the same material) and with a single detector element (i.e., 612a-d do not distinguish color). As described above, such devices rely on features of the emission signal other than spectral differences to identify incorporation events The filter module layer of the array illustrated in FIG. 12 comprises an absorptive filter layer within the reflective cone, and further includes a 2-color separation thin-film stack layer as part of the detector layer. The devices of this array therefore correspond most similarly to the device of FIG. 6, with a single filter layer 610 (i.e., 610a and 610b are the same material) and with a two-color detector element (i.e., the detector elements 612a and b are combined into a single element, and the detector elements 612c and d are combined into a single element, and the two combined elements have different color sensitivity). As described above, such devices rely both on the differences in the emission spectrum and on features of the emission signal other than spectral differences to identify incorporation events. As would be understood by one of ordinary skill in the art, the arrays illustrated in FIGS. 10-12 could be further modified to include alternative filter layers and detector elements, such as those shown in FIG. 6.

Figure 13:
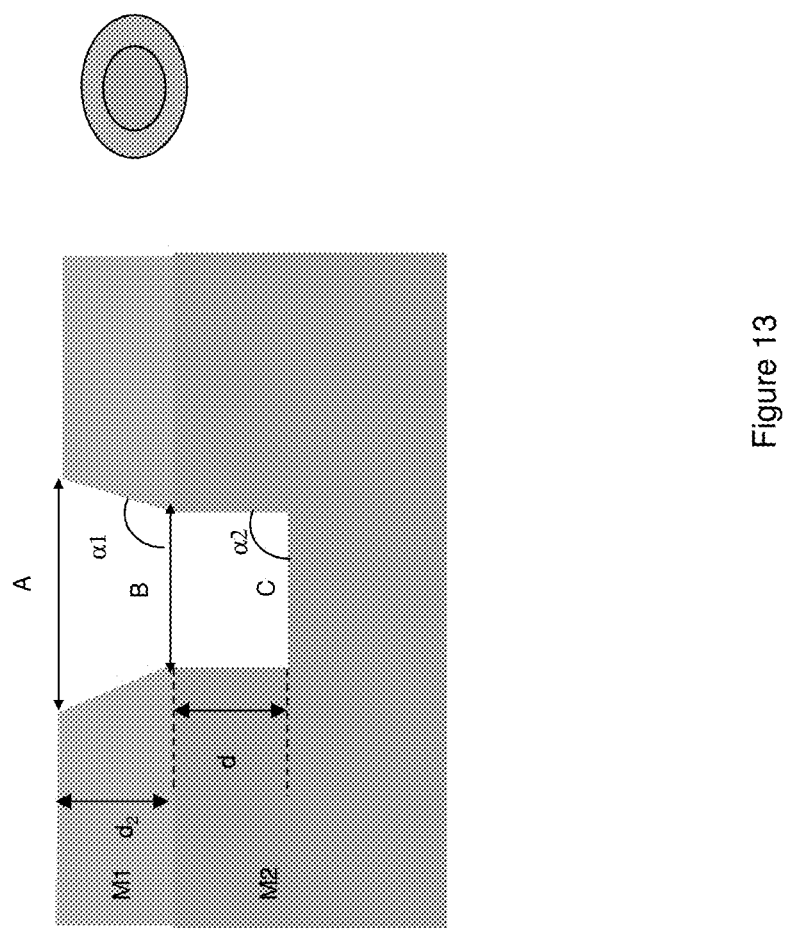
FIG. 13 schematically illustrates an exemplary ZMW module.

As noted above, the ZMWs of the devices of the instant arrays are nanometer-scale apertures that penetrate into the upper cladding of the waveguide module layer. For example, FIG. 13 illustrates an exemplary ZMW, wherein the ZMW material (M1) is deposited on the surface of the low refractive index ("low n") waveguide cladding layer (M2). M1 is typically a highly reflective metal and in preferred embodiments is aluminum. M2 is typically $SiO_2$ or another equivalent low n dielectric material. Distance $d_2$ is preferably from 50 to 150 nm and is most preferably approximately 100 nm. Distance d can range from 0 to 200 nm. In preferred embodiments, d is 100 nm±10%. In most preferred embodiments of the invention, d is 100 nm. The preferred angles of $\alpha 1$ and $\alpha 2$ are 101° and 95°, but other reasonable angles are within the scope of the invention. The ZMW pitch (the spacing between individual ZMWs) is preferably 6.7 um, but other reasonable values are within the scope of the invention. Specifically, the pitch may range from 2.5 to 8 um, depending on the camera and pixel selection. In addition, the overlay to cone (x,y,θ) is most preferably 150 nm, but a range of 20 to 200 nm is within the scope of the invention. Values for the distances A, B, and C are in some embodiments 200 nm, 160 nm, and 140 nm±15%. In preferred embodiments, the variability in these distances is as low as±5%. The inset drawing on the right side of FIG. 13 shows a schematic view of a typical ZMW, as viewed from above.

Figure 14:
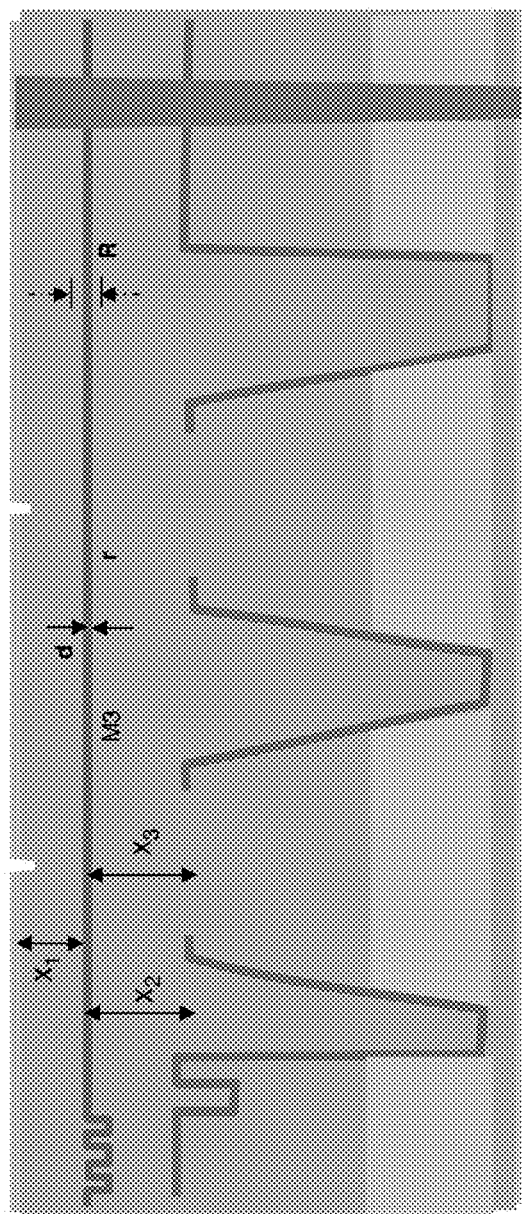
FIG. 14 schematically illustrates an exemplary array of integrated analytical devices, highlighting parameters relating to the waveguide module layer.

More specific details relating to the waveguide module layer of the instant arrays of integrated analytical devices are illustrated schematically in FIG. 14. Specifically, distances $X_1$, $X_2$, and $X_3$ are preferably 500 nm, 1000 nm, and 1200 nm, respectively, but values of 400 to 1500 nm for each of these parameters are considered within the scope of the invention. Distance d is preferably 50 nm but in some embodiments can range from 50 to 100 nm. The value for w (width into plane) is preferably 300 nm but can be as high as 1 um. The parameter, R, is the total range of waveguide thickness variation, which includes the thickness variation, side wall roughness of the waveguide (short scale <500 nm length), and the long range roughness of the waveguide (waviness at >10 um range). The overlay to ZMW (y, θ) is preferably 100 nm.

The material comprising the waveguide core, M3, is preferably silicon nitride ($Si_3N_4$, n(1.9)), but other materials, such as $Al_2O_3$ or other materials with high n (refractive index) and low autofluorescence are considered within the scope of the invention. As mentioned above, the waveguide core can be configured either in channels or as a planar waveguide, where the excitation illumination is propagated through the plane of the waveguide in two dimensions.

Figure 15:
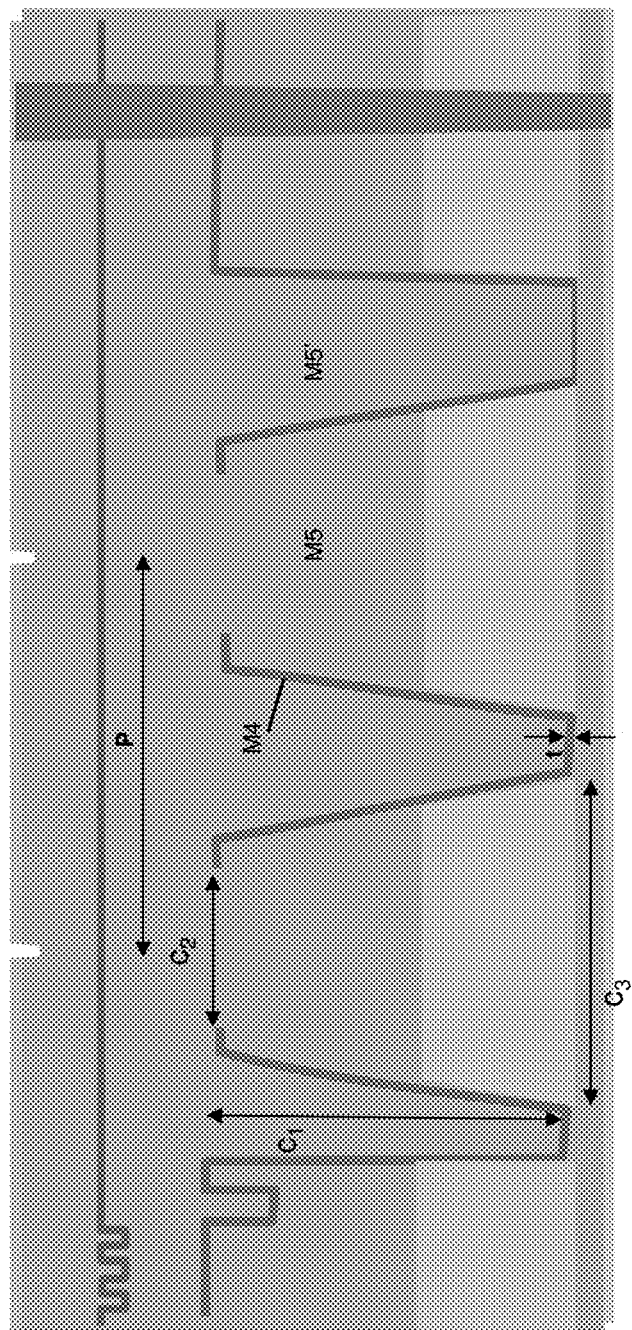
FIG. 15 schematically illustrates an exemplary array of integrated analytical devices, highlighting parameters relating to the collection module layer and reflective cones.

Parameters relating to the fabrication of the collection layer module and reflective cones are illustrated schematically in FIG. 15. Specifically, the distances $c_1$, $c_2$, and $c_3$ are preferably 6 um, 3 um, and 5.6 um, respectively, but other reasonable values for and variation in these distances are within the scope of the invention. The spacing, P, between ZMWs is preferably 6.7 um, but other reasonable values should be considered within the scope of the invention. Thickness t is 200 nm, but variation within this value is also understood to be within the scope of the invention. The material used in the reflective layer of the cone, M4, is preferably Al, but other reflective materials may be suitably substituted for this purpose. Likewise, the filler material within the cone, M5, and outside the cone, M5', is preferably an oxide or other suitable material, provided that the material is a low refractive index (low n) material and has low autofluorescence. M5 and M5' can be the same or different materials.

Figure 16:
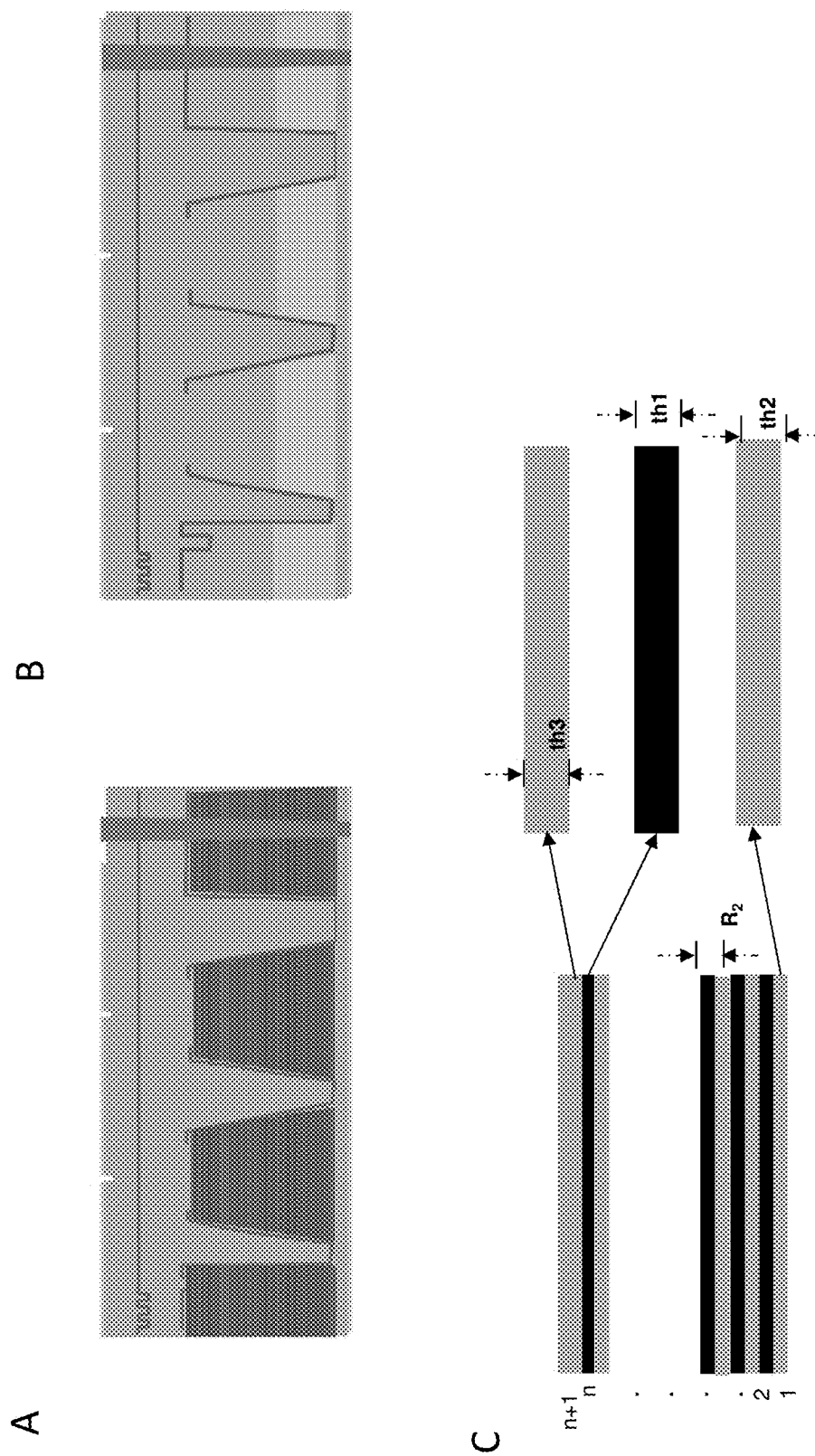
FIG. 16 schematically illustrates an exemplary array of integrated analytical devices, highlighting parameters relating to the filter module layer.

FIG. 16 provides a schematic illustration of the two preferred types of filter module layers: (A) a dielectric filter stack module and (B) an absorptive filter module. Panel (C) shows the composition of the filter stacks within the cones of the filter module layer of panel (A). Specifically, the filter stacks in the dielectric filter stack module are comprised of alternative layers of either GaP and $TiO_2$ or $TiO_2$ and $SiO_2$. For the GaP/$TiO_2$ design, the number of layers (n) is preferably 31, and the total thickness is preferably 1.2 um. The layer thicknesses are preferably 38 nm (th1) and 59 nm (th2), and the top (n+1) layer thickness is preferably 1.8 um (th3). For the $TiO_2$/$SiO_2$ design, the number of layers (n) is preferably 71, and the total thickness is preferably 6 um. The layer thicknesses are preferably 48 nm (th1) and 31 nm (th2). The long-range roughness, $R_2$, is preferably <5 nm. The absorptive filter of the filter layer module shown in the array of panel (B) is preferably composed of KMPR® MicroChem PR with total layers, n=1/2 um and Th1:2 um; Th2:3 um, but other materials with similar properties could be suitably substituted therefor. In all cases, the purpose of the filter module layer is to cut out stray light from the excitation illumination, typically any light at or below 532 nm in wavelength, and allow emission light above this wavelength to pass with minimal loss. Absent any color separation in the detector layer, the incorporation signals from the ZMW can thus be read by amplitude modulation or other non-spectral discrimination, as described in detail above.

Figure 17:
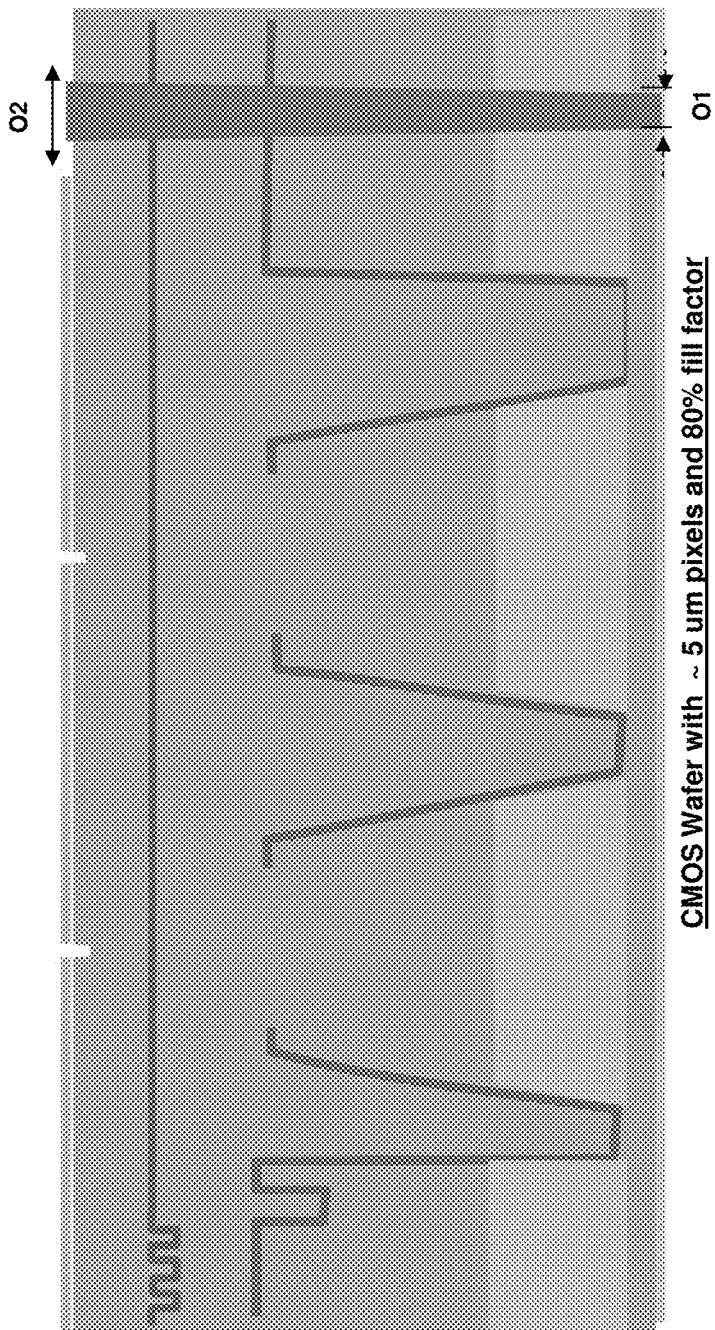
FIG. 17 schematically illustrates an exemplary array of integrated analytical devices, highlighting parameters relating to the deep trench opening module.

The deep trench opening module (1006, 1106, and 1206 of FIGS. 10-12, respectively) is illustrated schematically in FIG. 17. The trench fill material is preferably Al or Cu, but other suitable materials may be substituted. The deep trench can either be filled and then wire bonded or directly put through wire bonding using the above materials. The lower ($O_1$) and upper ($O_2$) dimensions are preferably 100 um and 150 um, but reasonable variation in these values is possible within the scope of the invention. The deep trench opening usefully provides access to the bond pads for the CMOS sensor.

Controlled ZMW Nanowell Dimensions

In another aspect, the instant disclosure provides arrays of integrated analytical devices wherein the dimensions of the ZMW nanowells are controlled by etching the upper cladding of the ZMW module layer until the nanowells fully penetrate into the upper cladding of the waveguide module layer, and then partially backfilling the etched nanowells. Also provided are methods for such control of the dimensions of the ZMW nanowells.

As previously described, the hole pattern for the ZMW nanowells is typically defined using an appropriate lithography tool, such as a 193 nm or 248 nm lithography node, and a photoresist material. Ideally, the nanowell is aligned as closely as possible to the underlying cone, or other collection feature, to ensure efficient transfer of emitted light signals from the ZMW to the associated detector feature and to minimize cross-talk. In some method embodiments disclosed herein, the nanowells are created using a timed reactive ion etch (RIE) on the patterned wafer. The RIE process is allowed to proceed for a predefined amount of time that is targeted to produce nanowells with a specified depth and distance from the underlying waveguides. Process variability in the RIE, as well as in the upstream processes, such as the cladding deposition, may, in some situations, result in a variation in the nanowell depth and distance from the waveguide, however, and alternative methods for controlling the dimension of the nanowell may be desirable in some circumstances.

Accordingly, in order to minimize variability in the nanowell dimensions, the nanowells may, in some embodiments, be constructed by allowing the RIE to proceed until the etching process fully penetrates the cladding material and exposes the waveguide. At this point, due to the difference in chemical composition of the waveguide compared to the cladding, the exposure of the waveguide material to the reaction chamber may generate an endpoint signal that is detectable by the processing tool and that can be used to terminate the RIE. Suitable selection of cladding and waveguide materials prevents significant etching or gouging of the waveguide and provides a strong endpoint signal. For example, in preferred embodiments, $SiO_2$ may be utilized for the cladding, and $Si_3N_4$ may be utilized for the waveguide. In alternative embodiments, an etch hardmask may be placed between the cladding and waveguide layers during the deposition of the cladding and waveguide stack in order to provide an endpoint signal or a resistance to the RIE, assuming that the hardmask used is optically compatible with the device. Suitable materials for the etch hardmask are well-known in the art.

Upon completion of the nanowell RIE process and the subsequent steps to remove etch residue and to clean the wafer, the nanowells may be partially backfilled with a well-controlled deposition process until the desired nanowell depth and distance to the waveguide is achieved. Low variability backfill processes are well known in the art, and their utilization may significantly reduce variances in the nanowell depth and distance from the waveguide. For example, atomic layer deposition (ALD) and low pressure chemical vapor deposition (LPCVD) are processes that can be very tightly controlled. The backfill material is preferably chosen to match the desired optical characteristics of the device. For example, the backfill material may in some embodiments be identical to the cladding material, although this is not a requirement. In addition, the pattern mask dimensions and as-etched nanowell dimensions are preferably specified to match the method of backfilling in order to achieve the desired final nanowell dimensions. For example, the required mask and as-etched nanowell dimensions may differ for a "conformal" deposition process, as compared to a "bottom-up" deposition process, as would be understood by those of ordinary skill in the art.

Lenses for Collimation and Redirection

In another aspect, the instant disclosure provides additional or alternative features within the collection module layer that improve the transmission of emission light from the ZMW nanowell to the detector. As described above, the collection module layer and the filter module layer are preferably fashioned in a cone shape that is defined by a reflective layer (see 1007, 1107, and 1207 in FIGS. 10, 11, and 12, respectively). The reflective layer covers the sides of the collection module layer and filter module layer of each integrated analytical device but provides an opening to allow emitted light to pass through. Such reflective cones improve the efficiency of capture of emitted light and minimize cross-talk between adjacent devices, as described, for example, in U.S. Patent Application Publication No. 2010/0099100, which is incorporated by reference herein in its entirety for all purposes. Parameters relating to the collection module layer and the reflective cones are illustrated in FIG. 15.

In some embodiments, it may be desirable to integrate one or more optical lenses into the collection module layer, either in combination with, or in place of, the reflective cones. Such optical lenses may serve to collimate and/or redirect light emitted from the ZMW. In particular, optical lenses are well suited for collimating emitted light with near on-axis rays, as well as splitting the emitted light, for example prior to color separation within the filter module layer. In addition, lenses are readily fabricated using standard techniques.

The integrated optical lenses of the instant devices may be either refractive lenses or diffractive lenses, depending on the optical and physical properties desired, as would be understood by those of ordinary skill in the art. Diffractive lenses may, in some circumstances, provide improved image quality, be more easily miniaturized, and/or be less expensive to fabricate than a comparable refractive lens. In some cases, the lenses may include separate refractive and diffractive components or may be hybrid lenses that combine both features in a single lens element.

In preferred embodiments, the integrated lenses of the instant analytical devices are integrated Fresnel lenses, which may also be known as zone plates or Fresnel zone plates when they function by diffraction rather than refraction or reflection. A Fresnel lens consists of a series of concentric rings with a specific tapered shape, or with alternating transparent and opaque zones (also called the Fresnel zones), with respect to the incident irradiation. These structures result in the focusing of light passing through the device by selective absorption or selective phase shifting and thus allow the device to function as a lens. The specific device design depends on the radiation to be focused, the refractive index of the material used to construct the lens, and the desired focal length, as is well known in the art. In some embodiments, the Fresnel lenses of the instant devices are refractive Fresnel lenses, in some embodiments, the Fresnel lenses are diffractive Fresnel lenses (or Fresnel zone plates), and in some embodiments, the Fresnel lenses combine refractive and diffractive features. In preferred embodiments, the Fresnel lenses are diffractive Fresnel lenses.

A variety of materials and methods may be used to fabricate Fresnel lenses, as is known in the art. For example, Fresnel lenses may be formed by the etching of zones in the planar surface of a material transparent to the light of interest and the subsequent deposition of an absorbing or phase shifting material into the etched zones. A phase Fresnel zone plate is a staircase approximation to a phase Fresnel lens. The efficiency of the phase Fresnel zone plate increases as the number of levels is increased. For example, a two-phase Fresnel zone plate can be shown to have a maximum diffraction efficiency of 40.5%, whereas a four-phase Fresnel zone plate has a maximum diffraction efficiency of 81%. Techniques for designing phase Fresnel zone plates with the desired characteristics are known in the art.

Fresnel lenses have been incorporated into advanced optical devices using various techniques, for example as imaging optics in illumination systems (see, e.g., U.S. Pat. No. 6,002,520), in light emitting devices (see, e.g., U.S. Pat. No. 6,987,613), in solid-state imaging devices (see, e.g, U.S. Pat. No. 7,499,094), in image sensors (see, e.g., U.S. Pat. No. 8,411,375), and in integrated infrared sensors (see, e.g., U.S. Patent Application Publication No. 2013/0043552). The design of the Fresnel lenses of the instant disclosure and their integration into the instant analytical device arrays may be achieved using analogous approaches.

In highly preferred embodiments, the Fresnel lens of the instant disclosure is a phase Fresnel zone plate.

Methods for Producing Arrays of Integrated Analytical Devices

In another aspect, the instant disclosure provides methods for producing arrays of integrated analytical devices. As described above, such arrays are useful, for example, in the large-scale sequencing of nucleic acids, such as, for example, genomic sequencing. Such arrays can be produced by a variety of methods. One preferred approach to producing the instant arrays involves the use of microfabrication methods such as semiconductor or MEMS processing methods, which have been highly developed for the production, for example, of integrated circuits. Similar processes have been used to create MEMS (micro electromechanical systems) for a variety of applications including inkjet printers, accelerometers, pressure transducers, and displays (such as digital micromirror displays (DMDs)). Microfabrication methods can be applied to a large substrate such as a wafer, which can later be diced into many devices, allowing for the production of many devices at one time.

The methods of the invention may, for example, apply resist processes, such as photoresists, to define structural elements on substrates or other layers. Etching processes may be used to produce three-dimensional structures, including component structures in the integrated analytical device. Deposition processes may be used to add layers onto the devices. Other semiconductor processes such as ashing, polishing, release, and liftoff may also be employed to create the structures of the invention, as described in more detail below.

For example, lithographic techniques may be used to define a mask layer out of polymeric materials, such as photoresists, using e.g., conventional photolithography, e-beam lithography, or the like. Alternatively, lithographic techniques may be applied in conjunction with layer deposition methods to deposit metal mask layers, e.g., using aluminum, gold, platinum, chrome, or other conventionally used metals, or other inorganic mask layers, e.g., silica based substrates such as silicon, $SiO_2$, or the like. Alternatively, negative tone processes may be employed to define pillars of resists that correspond to, for example, apertures. See, e.g., U.S. Pat. No. 7,170,050, which is incorporated by reference herein in its entirety for all purposes. The mask layer may then be deposited over the resist pillars and the pillars are subsequently removed. In particularly preferred aspects, both the underlying substrate and the mask layer are fabricated from the same material, which in particularly preferred aspects, is a transparent substrate material such as an $SiO_2$-based substrate such as glass, quartz, or fused silica. By providing the mask and underlying layers of the same material, one can ensure that the two layers have the same interactivity with the environments to which they are exposed, and thus minimize any hybrid surface interactions.

In the case of $SiO_2$-based substrates and mask layers, conventional fabrication processes may be employed. In particular, a glass substrate bearing the surface exposed waveguide has a layer of resist deposited over its surface. A negative of the mask layer is then defined by appropriate exposure and development of the resist layer to provide resist islands where one wishes to retain access to the underlying waveguide. The mask layer is then deposited over the surface and the remaining resist islands are removed, e.g., through a lift off process, to provide the openings to the underlying waveguides. In the case of metal layers, deposition may be accomplished through a number of means, including evaporation, sputtering or the like. Such processes are described in, e.g., U.S. Pat. No. 7,170,050. In the case of silica based mask layers, a chemical vapor deposition (CVD) process may be employed to deposit a silicon layer onto the surface. Following lift off of the resist layer, a thermal oxidation process can convert the mask layer to $SiO_2$. Alternatively, etching methods may be used to etch access points to underlying layers using conventional processes. For example, a silicon layer may be deposited over an underlying substrate. A resist layer is then deposited over the surface of the silicon layer and exposed and developed to define the pattern of the mask. The access points are then etched from the silicon layer using an appropriate differential etch to remove silicon but not the underlying $SiO_2$ substrate. Once the mask layer is defined, the silicon layer is again converted to $SiO_2$ using, e.g., a thermal oxidation process.

One aspect of the invention relates to a process for producing arrays of integrated analytical devices comprising the steps of: providing a substrate layer; depositing a filter module layer on the substrate layer; depositing a collection module layer on the filter module layer; patterning and etching the filter module layer and collection module layer to form an array of protrusions having tops and sides and having gaps between the protrusions; depositing a reflective material on the array of protrusions such that the tops and sides of the protrusions comprise a reflective layer; depositing a fill material on the reflective layer such that the fill material fills the gaps between the protrusions; patterning and etching the fill material and reflective layer to remove the reflective layer from the tops of the protrusions; depositing a first layer of low n material on the etched fill material and the tops of the protrusions; depositing a high n material on the first layer of low n material; depositing a second layer of low n material on the high n material to form an upper cladding and to complete a waveguide module layer disposed on the collection module layer; depositing a zero-mode waveguide material on the surface of the waveguide module layer; and patterning and etching the zero-mode waveguide material to define an array of nanometer-scale apertures penetrating into the upper cladding of the waveguide module layer. Unless specifically described, the order of the steps of the processes described herein can be altered, where suitable, and, in some cases, steps may be omitted or added.

For example, in some embodiments, the instant fabrication processes may include steps to generate arrays with collection module layers that comprise one or more integrated lenses, such as Fresnel lenses. In such arrays, the integrated lenses may, in certain embodiments, take the place of the reflective layer, for example the cone-shaped reflective layer (1007, 1107, and 1207) of FIGS. 10-12. In some embodiments, however, the instant fabrication processes may be used to generate integrated analytical devices comprising both one or more integrated lenses and a reflective layer.

One semiconductor fabrication process according an aspect of the instant invention is shown in FIGS. 18A and 18B, which illustrates the fabrication of an array of integrated analytical devices comprising a dielectric filter stack in the cone between the collection layer and the detection layer. An alternative fabrication process, as illustrated in FIGS. 19A and 19B, results in an array of integrated analytical devices comprising an absorptive filter stack in the cone between the collection layer and the detection layer of the device.

In each of the above exemplary approaches, the process begins with a clean substrate layer. The substrate layer used in the instant methods of production may be of any suitable rigid material. The substrate layer material may comprise, for example, an inorganic oxide material such as silica. A preferred material is a detector layer, such as, for example, a CMOS wafer, i.e., a wafer made up of CMOS sensors or CCD arrays. See, for example, *CMOS Imagers From Phototransduction to Image Processing* (2004) Yadid-Pecht and Etienne-Cummings, eds.; Springer; *CMOS/CCD Sensors and Camera Systems* (2007) Holst and Lomheim; SPIE Press.

The surface of the substrate may be prepared for deposition by, for example, a $H_2O_2$, low HF dip, or another type of oxide-friendly cleaning step. The second step involves a passivation deposition step, for example by plasma-enhanced chemical vapor deposition (PECVD) of silicon oxynitride (SiON). This step may also optionally reduce the topography of the layer. Furthermore, this step may be substituted for different filter layers, as shown in more detail in the variant process flow steps of FIG. 20.

As shown in FIG. 18A, for the fabrication of an array of integrated analytical devices comprising a dielectric filter stack, the next step preferably involves deposition of a dielectric filter layer, preferably by atomic layer deposition. In preferred embodiments, the filter stacks are $TiO_2$ and $SiO_2$ or GaP and $TiO_2$, as described above and illustrated in FIG. 16B. In the alternative process flow of FIGS. 19A and B, for the fabrication of an array of integrated analytical devices comprising an absorptive filter, the next step involves deposition of an absorptive filter layer, preferably by spin coat deposition of an epoxy resin, such as KMPR® MicroChem photoresist, or another low autofluorescence resist. In each case, and as described above, the filter layer acts to block source light at 532 nm and below.

Following deposition of the filter layer, the remaining steps in the process flows of FIGS. 18 and 19, and the variant of FIG. 20, are similar. Specifically, a collection module layer is formed on the surface of the filter module layer, preferably by the deposition of $SiO_2$, or another suitable low-loss material, using PECVD techniques. The step may, in some embodiments, be omitted, for example if the filter layer of the device completely fills the reflective cone. The material may, in some embodiments, match the material of the bottom cladding in the waveguide module layer, or it may, in other embodiments, be different.

The patterns of the cones are then defined using an appropriate lithography node, such as I-line or 248 nm node. Following the patterning step, the cones are etched using an appropriate chemistry (e.g., F chemistry for oxide, ion milling for absorptive filters, etc.). Specific variations in the etching step, such as methods to adjust the slope of the cones and to minimize autofluorescence of the etched material, may be found, for example, in U.S. Patent Application Publication No. 2010/0099100. In some embodiments of the invention, the order of the filter deposition and collection cone deposition steps may be reversed. The system may be optimized to provide better performance, for example by altering the location of the filter in the cone, within the scope of the invention, as would be understood by one of ordinary skill in the art.

Following the cone etching step, a reflective layer is deposited, preferably by sputter deposition. The material used in the reflective layer is typically a highly reflective metal, and in preferred embodiments is aluminum, gold, or chromium. In some embodiments, deposition or metallization is accomplished using a conformal deposition process, e.g. evaporation.

Following deposition of the reflective layer, the gaps between the cones are filled, preferably using a spin-coat process or PECVD. The material used to fill the gaps may be chosen depending on the desired function. For example, the material may provide a further absorptive filter function, may provide the bottom cladding for the waveguide module layer, or may provide a combination of functions. Preferably, the fill material has low autofluorescence and is planarizing. A variety of fill materials may be employed for this step, including additional metal layers (or continuous metal layers), inorganic materials, such as silicon, silicon dioxide, polymeric materials, semiconductor materials, or the like. In particularly preferred aspects, a silica based layer is deposited as the fill layer, and preferably the layer comprises silicon dioxide or other glass-like material. Production of a glass fill layer may be accomplished through a number of conventional processes, including the use of spin-on glass materials, such as silsesquioxanes, or through the vapor deposition and subsequent oxidation of silicon fill layers over the substrate.

The surface of the array is next subjected to reverse etch patterning, preferably using an I-line process with a photoresist material. The resulting reverse mask creates a pattern between the mirrored surfaces, which is subsequently etched using an appropriate chemistry (e.g., F chemistry for oxide, $O_2$ for epoxy resin, etc.) as would be understood in the art. Methods suitable for the etching step may be found, for example, in U.S. Patent Application Publication No. 2010/0099100.

The etched surface is next subjected to a planarization step to planarize topography and remove excess oxide from the top of cone structures. The planarization layer may be a hard material such as a spin-on glass, or may be a soft planarization layer. The soft planarization layer may be, for example, a spin-on UV curable organic polymer such as Summers J91 or SK9. Where the planarization layer comprises a hard material, the planarization is generally polished, for example with chemical mechanical planarization (CMP). Where the planarization layer comprises a soft material, such as a UV cure polymer, then after UV cure, oxygen etch may be used to etch away the top region of the spin-on polymer, analogous to polishing. In some embodiments, the steps of gap fill deposition, reverse etch patterning, reverse pattern etching, and planarization may looped iteratively until suitable planarization is achieved.

The planarized surface is next subjected to a pattern definition for top flat mirror etch (TFME) step, preferably using an appropriate lithography node, such as an I-line process, and a photoresist material. The surface is next subjected to a top flat mirror etch (TFME) step, etching a combination of oxide and reflective material, such as Al or Au to uncover the cone layer.

The bottom clad of the waveguide module layer is next deposited, preferably using spin-coat, PECVD, or other suitable methods or combination of methods. The material deposited is preferably a material having low autofluorescence and low k, such as a low k spin-on dielectric (SOD), SiO2. The deposited surface functions as the cladding for the waveguide.

The core of the waveguide is then deposited, using plasma-enhanced chemical vapor deposition, atomic layer deposition, or other suitable techniques or combinations. The core is deposited using a material of low autofluorescence and high k, such as $Si_3N_4$, $Al_2O_3$, or others. In some embodiments, a waveguide coupler is created on the surface prior to depositing of the core of the waveguide using a pattern/etch loop. The coupler and core are deposited using the same material. The pattern for the waveguide is next defined using an appropriate lithography node, such as I-line or 248 nm node, and a photoresist material. For example, a 300 nm at 5 micro pitch would be a channel waveguide. In some embodiments, dummy waveguides are placed between the functional waveguides. In some embodiments, slab waveguides are provided.

The top clad of the waveguide is then deposited by spin-coat, PECVD, or other suitable methods, preferably using a material having low autofluorescence and low k, such as a low k spin-on dielectric (SOD), SiO2. A confinement material, such as Al or other highly reflective and low loss material, is next deposited on the surface by, for example, physical vapor deposition (PVD).

The hole pattern for the ZMW nanowells is next defined using an appropriate lithography tool, such as a 193 nm or 248 nm lithography node, and a photoresist material. The nanowell is aligned as closely as possible to the underlying cone to ensure efficient transfer of emitted signals from the ZMW and to minimize cross-talk. The nanowell is next etched, preferably using a 2-stage process. The nanowell is etched into the confinement material and the top clad. Suitable materials include, for example, Al, SOG, and $SiO_2$.

The deep trench of some embodiments of the instant arrays is formed by pattern definition and etching steps using standard methods and materials.

After all other process flow steps are complete, the arrays are treated to remove all residues using a cleaning process step.

As noted above, the detector layer in the integrated analytical devices of the instant disclosure may include a filter stack to achieve color separation, for example as shown in detector layer 612 of FIG. 6 and in detector layer 1205 of FIG. 12. In some embodiments of the instant integrated analytical devices, color separation may provide further signal information about the incorporation step of the sequencing reaction. As shown in FIG. 20, the process flows of FIGS. 18 and 19 may be modified to allow for the incorporation of color-separation filters in the detector layer of an integrated analytical device. In particular, the process flow steps shown in FIG. 20 may be used in place of steps 1-3 of FIGS. 18 and 19. In other words, a 2-color separation device would be generated by following steps 1-8 of FIG. 20 and continuing on with the collection cone deposition, step 4, of FIGS. 18 and 19.

As mentioned above, the methods of the invention in some cases use resists for defining and producing structures with lithography. These resists can be, for example, photoresists or e-beam resists. The photoresists can be developed using UV, deep UV, G-line, H-line, I-line or other suitable wavelength or set of wavelengths. The type of resist that is used, and therefore the type of instrumentation that is employed for processing, will depend on the dimensions of the features that are created. In many processes described herein, higher resolution resists and equipment will be used for the production of the aperture which corresponds to the reaction volume, where the size of the aperture may be on the order of 10 nm to 500 nm, and a lower resolution resist and associated instrumentation is used for the creation of the rest of the integrated analytical device, which may have features on the dimensions of 1 micron to 20 microns. Many resists are known in the art, and many are available commercially from companies such as Rohm and Haas and Shipley. The resists used in the processes of the invention may be negative or positive photoresists. Where a process is described herein using a negative photoresist, it is to be understood that a suitable positive photoresist may also be employed where practical, and vice versa. Where appropriate, chemical amplification may also be employed in order to increase the sensitivity of the resist. The removal of the resist, the cleaning, rinsing, ashing, and drying of the substrate may be performed as appropriate and as taught and known in the art.

In some cases, the tools used for photolithography of the reaction region (e.g. ZMW) use photolithography exposure tool capable of creating structures having feature sizes of about of 10 nm to about 100 nm. Such systems include, for example, an AMSL XT1250 exposure tool.

Etching processes are used in some aspects of the invention in order to produce the three dimensional features in a substrate or in other layers, to fashion, for example, optical elements or lenses, or reaction volumes such as nanoscale apertures. The etching process that is used will depend on the type of material used, the dimensions of the features, and the resist system. In some cases wet etching or wet chemical etching is employed. Electrochemical etching may also be employed. In some embodiments plasma etching or reactive ion etching (RIE) is used as an etching process. Deep reactive ion etching (DRIE) may also be employed, for example, where structures having high aspect ratio are desired. Dry vapor phase etching, for example with xenon difluoride, may also be used. Bulk micromachining or surface micromachining may be used as appropriate to create the device structures of the disclosure. The etching used in the methods of the disclosure may be gray-scale etching. The conditions of the resist formation and etching are controlled to produce side walls having the desired geometries, such as having the desired side-wall angle.

Some processes of the invention involve the deposition of reflective layers, or cladding layers. The deposition of these reflective layers may be accomplished by wet processes including spinning on layers from solution, or by gas-phase processes. Suitable processes include electroplating, sputter deposition, physical vapor deposition, evaporation, molecular beam epitaxy, atomic layer deposition, and chemical vapor deposition. Metals may be used as the reflective layer and the cladding layer. Suitable metals include gold, nickel, aluminum, chromium, titanium, platinum, and silver. The reflective and/or cladding layers may comprise aluminum, which may be deposited by sputtering, for example using a commercially available sputter tool available from CVC, Novellus, or MRC.

Where layers are deposited during the processes of the invention, in some cases, the layers are treated before moving on to the next step in the process. For example, the deposited layer may be annealed, planarized, cleaned, passivated, or lightly etched in order to improve its properties.

In some methods of the invention, protective layers or sacrificial layers are deposited. The protective layers may be polymeric layers, or may be inorganic layers. Suitable protective or sacrificial layers include germanium (Ge) and amorphous silicon (a-Si). Protective layers may be used to produce features as described herein. The type of material for the protective or sacrificial layer may be chosen for its selective reactivity, for example to wet chemical etchants. For example, in some cases, the ability to selectively etch germanium with heated hydrogen peroxide in the presence of silicon dioxide and aluminum results in its being utilized to produce optical structures combined with nanoscale apertures.

In some processes, a pull-back process may be employed. A pull-back process generally involves etching in from the edges of a feature within a layer in order to reduce the dimensions of the feature. Pull-back may be performed using a wet chemical reagent that selectively reacts with a layer which has exposed edges. In some cases a germanium layer is pulled back using hydrogen peroxide.

Some methods employ a polishing step to remove a surface region from a surface. Suitable methods include chemical-mechanical polishing or chemical-mechanical planarization (CMP).

Some methods of the invention incorporate a planarization layer. The method for depositing the planarization layer depends on the type of material that is used. The planarization layer may be a hard material, such as an inorganic material, for example silicon nitride; it may be a metallic material such as aluminum; or it may be a soft material, such as a polymeric material, e.g. an organic or silicon based polymer. The planarization layer may be a glass, such as a silicon dioxide material. In some cases, the planarization layer comprises a spin-on glass such as a silicate, phosphosilicate or siloxane material. Suitable spin-on glass materials are available, for example, from Honeywell Corporation. The planarization layer may comprise, for example, a glass doped with other agents to control its melting properties, such a boro-phosphoro-silicate glass (BPSG). Suitable polymeric planarization materials include, for example, polyimides.

After the arrays of the instant disclosure are complete, such as by, for example, following the process flows of FIG. 18 or 19, and optionally the variant steps recited in FIG. 20, the arrays may be further processed, such as, for example, by separating the arrays into individual chips and readying them for sequencing. The further processing steps will depend on the situation but may typically include the following treatments: surface treatment (a series of wet/vapor phase treatments to put down a specific surface that attracts the DNA polymerase enzyme to the bottom of the nanowell); stacking (a process to protect the top surface of the surface-treated device wafer and, in some cases, creating a well for the sequencing mixture); thinning (a process in which the composite top-plated and surface-treated device wafer may be thinned—including grinding lapping, polishing, or other treatments); dicing (a process in which the composite wafer is divided into individual chips using a standard semiconductor dicing saw); and packaging (a process involving a standard pick and place tool to mount the chips onto a substrate and create electrical/optical outputs for data collection). These further processing steps are either known in the art or are disclosed in references such as U.S. Patent Application Publication Nos. 2008/0176769 and 2011/0183409, which are incorporated by reference herein in their entireties for all purposes.

As just noted, the arrays of the invention may be incorporated into analysis systems for analyzing the multiple reactions occurring in the reaction regions of the array. The arrays described herein typically have reaction regions that are accessible to fluid from the top, and that are accessible for optical analysis from the bottom. The arrays are thus generally incorporated into a vessel into which a reaction mixture of interest is introduced. In some cases, the individual reaction regions are all in contact with one volume of fluid, which may have, for example, multiple nucleic acid template molecules which may be analyzed, and which may have the nucleotides, cofactors, and other additives for carrying out the reaction to be analyzed.

The vessel that comprises the array may be placed within an instrument which has the appropriate optical components, computer controls, and data analysis systems. The vessel comprising the array will be held within the instrument such that the reaction conditions, such as the vessel temperature and vessel atmospheric conditions can be controlled. The vessel atmospheric conditions may comprise the makeup of the gas above the sample, for example the humidity, and the level of other gaseous species such as oxygen.

Other Aspects

In some aspects, the instant disclosure provides arrays, analytical devices, and methods according to the following numbered paragraphs.

1. An array of integrated analytical devices comprising:
   a substrate layer;
   a filter module layer disposed on the substrate layer;
   a collection module layer disposed on or with the filter module layer;
   a waveguide module layer disposed on the collection module layer;
   a zero-mode waveguide module layer disposed on the waveguide module layer;
   wherein the zero-mode waveguide module layer comprises at least one nanometer-scale aperture penetrating into the waveguide module layer.
2. The analytical device of paragraph 1, wherein the substrate layer is a detector layer.
3. The analytical device of paragraph 1, wherein the substrate layer is a CMOS wafer.
4. The analytical device of paragraph 1, wherein the filter module layer comprises a dielectric filter.
5. The analytical device of paragraph 1, wherein the filter module layer comprises an absorptive filter.
6. The analytical device of paragraph 1, wherein the detector layer comprises a color-separation layer.
7. A method for producing an array of integrated analytical devices comprising:
   providing a substrate layer;
   depositing a filter module layer on the substrate layer;
   depositing a collection module layer on the filter module layer;
   patterning and etching the filter module layer and the collection module layer to form an array of protrusions having tops and sides and having gaps between the protrusions;
   depositing a reflective material on the array of protrusions such that the tops and sides of the protrusions comprise a reflective layer;
   depositing a fill material on the reflective layer such that the fill material fills the gaps between the protrusions;
   patterning and etching the fill material and reflective layer to remove the reflective layer from the tops of the protrusions;
   depositing a first layer of low n material on the etched fill material and the tops of the protrusions;
   depositing a high n material on the first layer of low n material;
   depositing a second layer of low n material on the high n material to form an upper cladding and to complete a waveguide module layer disposed on the collection module layer;
   depositing a zero-mode waveguide material on the surface of the waveguide module layer;
   patterning and etching the zero-mode waveguide material to define an array of nanometer-scale apertures penetrating into the upper cladding of the waveguide module layer.
8. The method of paragraph 7, further comprising the step of patterning and etching the high n material to define a waveguide.
9. The method of paragraph 7, wherein the substrate layer is a detector layer.
10. The method of paragraph 7, wherein the substrate layer is a CMOS wafer.
11. The method of paragraph 7, wherein the filter module layer comprises a dielectric filter.
12. The method of paragraph 7, wherein the filter module layer comprises an absorptive filter.
13. The method of paragraph 7, wherein the substrate layer comprises a color-separation layer.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. A method of nucleic acid sequencing comprising the steps of:
providing an array of integrated analytical devices, wherein at least one integrated analytical device in the array of integrated analytical devices comprises a nucleic acid template/polymerase primer complex immobilized within an optically confined region, a plurality of fluorescently labeled nucleotides in fluid contact with the nucleic acid template/polymerase primer complex, and a single detector element optically coupled to the optically confined region, wherein the optically confined region is in a nanowell that is illuminated by an optical excitation waveguide, and wherein at least two fluorescently labeled nucleotides of the plurality of fluorescently labeled nucleotides emit fluorescence of different intensities at an emission wavelength;
illuminating the optically confined region with an excitation wavelength;
measuring a fluorescent signal from the optically confined region at the single detector element; and
identifying at least one of the at least two fluorescently labeled nucleotides by an intensity of the measured fluorescent signal at the emission wavelength.

2. The method of claim 1, wherein the array of integrated analytical devices comprises:
a substrate layer, wherein the substrate layer is a detector layer comprising the single detector element;
a waveguide module layer disposed above the substrate layer, wherein the waveguide module layer comprises the optical excitation waveguide; and
a zero-mode waveguide module layer disposed on the waveguide module layer, wherein the zero-mode waveguide module layer comprises a plurality of nanowells penetrating to the waveguide module layer.

3. The method of claim 2, wherein the detector layer is a CMOS wafer.

4. The method of claim 2, wherein the single detector element comprises one pixel.

5. The method of claim 2, wherein the array does not comprise a color separation layer.

6. The method of claim 2, wherein the optical excitation waveguide comprises an upper waveguide cladding material that is $SiO_2$.

7. The method of claim 2, wherein the optical excitation waveguide comprises a waveguide core material that is $Si_3N_4$.

8. The method of claim 2, wherein the array comprises at least 100 analytical devices.

9. The method of claim 2, wherein the array has a density of at least 1000 apertures per $cm^2$.

10. The method of claim 2, wherein the array further comprises a filter module layer disposed between the detector layer and the waveguide module layer.

11. The method of claim 10, wherein the filter module layer comprises a dielectric filter.

12. The method of claim 10, wherein the filter module layer comprises an absorptive filter.

13. The method of claim 2, wherein the plurality of nanowells is formed by etching.

14. The method of claim 2, wherein at least one nanowell fully penetrates an upper waveguide cladding material.

15. The method of claim 14 wherein the at least one nanowell is a partially backfilled nanowell.

16. The method of claim 2, wherein the array of integrated analytical devices further comprising an etch hardmask.

17. The method of claim 1, wherein the array of integrated analytical devices is associated with an excitation light source.

18. The method of claim 17, wherein the excitation light source is coupled to the array of integrated analytical devices through an optical coupler integrated in the array.

19. The method of claim 17, wherein the excitation light source comprises a single excitation source.

* * * * *